(12) United States Patent
Lycke et al.

(10) Patent No.: US 7,452,982 B2
(45) Date of Patent: Nov. 18, 2008

(54) IMMUNOGENIC COMPLEX

(75) Inventors: Nils Lycke, Savedalen (SE); Kristian Dalsgaard, Kalvehave (DK); Allan Mc Mowat, Glasgow (GB); Bjorn Lowenadler, Askim (SE); Peter Kaastrup, Maaloev (DK)

(73) Assignee: Arexis AB, Molndal (SE)

( * ) Notice: Subject to any disclaimer, the term of this patent is extended or adjusted under 35 U.S.C. 154(b) by 252 days.

(21) Appl. No.: 10/381,882

(22) PCT Filed: Oct. 1, 2001

(86) PCT No.: PCT/SE01/02117

§ 371 (c)(1),
(2), (4) Date: Aug. 19, 2003

(87) PCT Pub. No.: WO02/26255

PCT Pub. Date: Apr. 4, 2002

(65) Prior Publication Data

US 2004/0052815 A1    Mar. 18, 2004

(30) Foreign Application Priority Data

Sep. 29, 2000    (SE) .................................. 0003538

(51) Int. Cl.
*C07K 1/00* (2006.01)
*C07K 14/00* (2006.01)
*C07K 16/00* (2006.01)
*C07K 17/00* (2006.01)
*C08H 1/00* (2006.01)
*A61K 39/385* (2006.01)
*A61K 45/00* (2006.01)

(52) U.S. Cl. .................... 530/403; 530/350; 424/282.1; 424/197.11

(58) Field of Classification Search ....................... None
See application file for complete search history.

(56) References Cited

U.S. PATENT DOCUMENTS

| 5,492,694 A | 2/1996 | Nagaraja et al. |
| 5,688,772 A | 11/1997 | Estrada et al. |
| 5,736,139 A | 4/1998 | Kink et al. |
| 5,917,026 A | 6/1999 | Löwenadler et al. |
| 6,027,732 A * | 2/2000 | Morein et al. ............ 424/241.1 |

OTHER PUBLICATIONS

Mowat et al., 1999, Immunology Letters, vol. 65: 133-140.*
Agren et al., 1997, J. Immunol. vol. 158:3936-3946.*
Sultan et al., 1998, Inf. and Immun. vol. 66: 462-468.*
Allan McI Mowatt et al., "Oral Vaccination with Immune Stimulating Complexes," Immunology Letters, V. 65, 1999, pp. 133-140.
Christin Andersson et al., "General Expression Vectors for Production of Hydrophobically Tagged Immunogens for Direct Iscom Incorporation," Journal of Immunological Methods, V. 222, 1999, pp. 171-182.
Lena C. Ågren et al., "Adjuvanticity of the Cholera Toxin A1-Based Gene Fusion Protein, CTA1-DD, is Critically Dependent on the ADP-Ribosyltransferase and Ig-Binding Activity," Journal of Immunology, V. 162, 1999, pp. 2432-2440.

* cited by examiner

*Primary Examiner*—G. R. Ewoldt
*Assistant Examiner*—Amy E Juedes
(74) *Attorney, Agent, or Firm*—Young & Thompson

(57) ABSTRACT

The invention relates to an immunogenic complex comprising at a least one glycoside and at least one lipid, integrated into an iscom complex or matrix, and at least one antigen which antigen is integrated into the iscom complex or coupled on to or mixed with the iscom complex or iscom matrix complex, characterised in that it also comprises at least one enzyme. It also relates to such a complex further comprising at least one peptide which specifically binds to a receptor expressed on a cell capable of antigen presentation, which cell expresses MHC Class I or Class II and to compositions comprising the complexes.

13 Claims, 21 Drawing Sheets

Figure 6B

Figure 1:
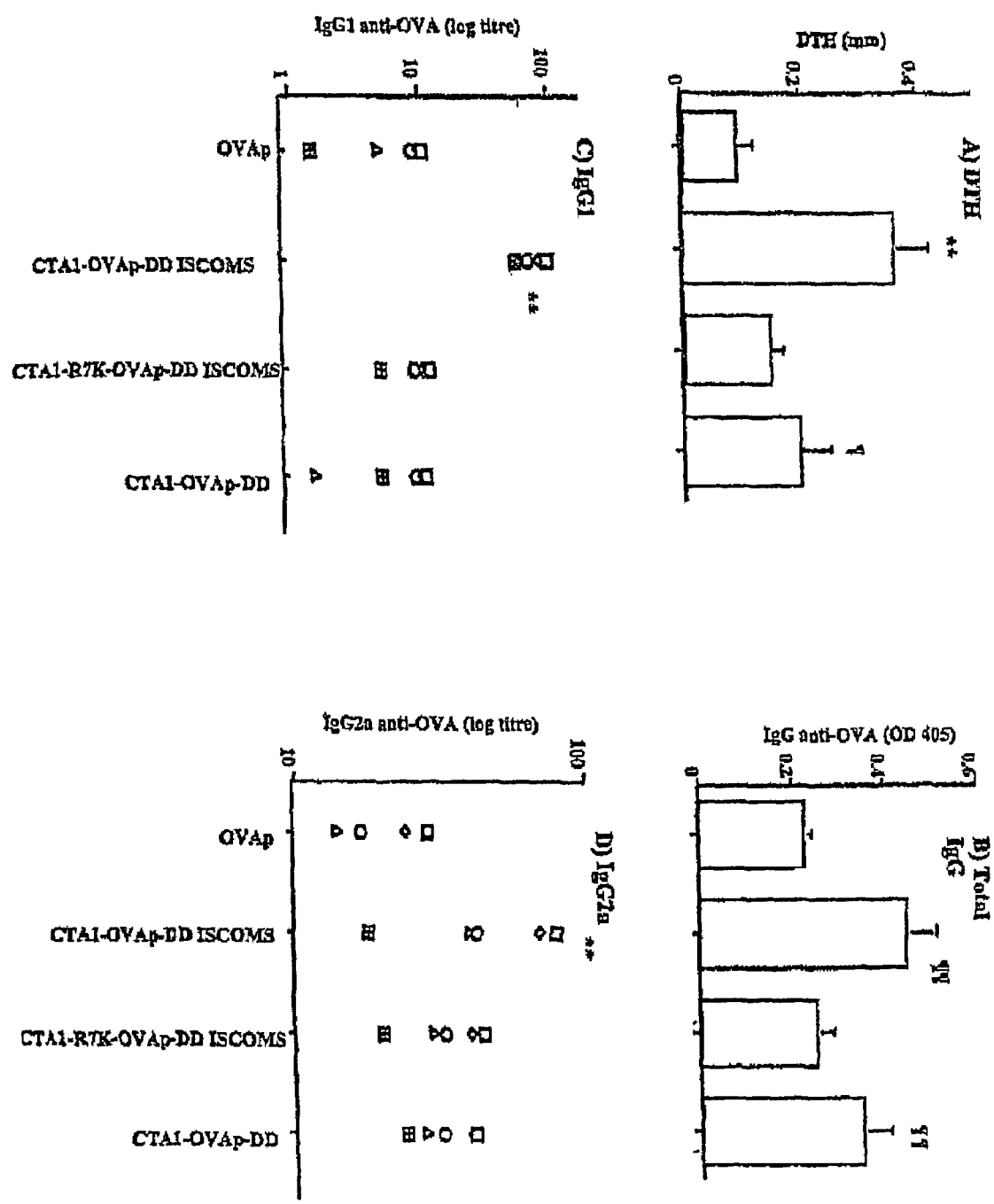

```
(Linear) MAP of: ctalr7k-ova-dd.seq   check: 1131   from: 1 to: 3798
CTA1-DD expressionsvektor
With 217 enzymes: *
MaxCuts: 1

April 30, 1999 11:10
Writing
            GTGCCTCACTGATTAAGCATTGGTAACTGTCAGACCAAGTTTACTCATATATACTTTAGA
       1    ------------+------------+------------+------------+------------+------------+  60
            CACGGAGTGACTAATTCGTAACCATTGACAGTCTGGTTCAAATGAGTATATATGAAATCT a         V  P  H  *  L  S  I  G  N  C  Q  T  K  F  T  H  I  Y  F  R   -
    b           C  L  T  D  *  A  L  V  T  V  R  P  S  L  L  I  Y  T  L  D -
    c             A  S  L  I  K  H  W  *  L  S  D  Q  V  Y  S  Y  I  L  *  I -

TTGATTTAAAACTTCATTTTTAATTTAAAAGGATCTAGGTGAAGATCCTTTTTGATAATC
       61   ------------+------------+------------+------------+------------+------------+ 120
            AACTAAATTTTGAAGTAAAAATTAAATTTTCCTAGATCCACTTCTAGGAAAAACTATTAG a         L  I  *  N  F  F  N  L  K  G  S  R  *  R  S  F  L  I  I    -
    b           *  F  K  T  S  F  L  I  *  K  D  L  G  E  D  P  F  *  *  S  -
    c             D  L  K  L  H  F  *  F  K  R  I  *  V  K  I  L  F  D  N  L -

TCATGACCAAAATCCCTTAACGTGAGTTTTCGTTCCACTGAGCGTCAGACCCCGTAGAAA
       121  ------------+------------+------------+------------+------------+------------+ 180
            AGTACTGGTTTTAGGGAATTGCACTCAAAAGCAAGGTGACTCGCAGTCTGGGGCATCTTT a         S  *  P  K  S  L  N  V  S  F  R  S  T  E  R  Q  T  P  *  K   -
    b           H  D  Q  N  P  L  T  *  V  F  V  P  L  S  V  R  P  R  R  K  -
    c             M  T  K  I  P  *  R  E  F  S  F  H  *  A  S  D  P  V  E  K -

AGATCAAAGGATCTTCTTGAGATCCTTTTTTTCTGCGCGTAATCTGCTGCTTGCAAACAA
       181  ------------+------------+------------+------------+------------+------------+ 240
            TCTAGTTTCCTAGAAGAACTCTAGGAAAAAAAGACGCGCATTAGACGACGAACGTTTGTT a         R  S  K  D  L  L  E  I  L  F  F  C  A  *  S  A  A  C  K  Q   -
    b           D  Q  R  I  F  L  R  S  F  F  S  A  R  N  L  L  L  A  N  K  -
    c             I  K  G  S  S  *  D  P  F  F  L  R  V  I  C  C  L  Q  T  K -

HgiEII                                              Eco57I
                              |                                                   |
            AAAAACCACCGCTACCAGCGGTGGTTTGTTTGCCGGATCAAGAGCTACCAACTCTTTTTC
       241  ------------+------------+------------+------------+------------+------------+ 300
            TTTTTGGTGGCGATGGTCGCCACCAAACAAACGGCCTAGTTCTCGATGGTTGAGAAAAAG a         K  N  H  R  Y  Q  R  W  F  V  C  R  I  K  S  Y  Q  L  F  F   -
    b           K  T  T  A  T  S  G  G  L  F  A  G  S  R  A  T  N  S  F  S  -
    c             K  P  P  L  P  A  V  V  C  L  P  D  Q  E  L  P  T  L  F  P -

CGAAGGTAACTGGCTTCAGCAGAGCGCAGATACCAAATACTGTCCTTCTAGTGTAGCCGT
       301  ------------+------------+------------+------------+------------+------------+ 360
            GCTTCCATTGACCGAAGTCGTCTCGCGTCTATGGTTTATGACAGGAAGATCACATCGGCA a         R  R  *  L  A  S  A  E  R  R  Y  Q  I  L  S  F  *  C  S  R   -
```

Figure 7 (cont.)

```
b         E  G  N  W  L  Q  Q  S  A  D  T  K  Y  C  P  S  S  V  A  V  -
c            K  V  T  G  F  S  R  A  Q  I  P  N  T  V  L  L  V  *  P  *  -

AGTTAGGCCACCACTTCAAGAACTCTGTAGCACCGCCTACATACCTCGCTCTGCTAATCC
    361    ------+---------+---------+---------+---------+---------+ 420
           TCAATCCGGTGGTGAAGTTCTTGAGACATCGTGGCGGATGTATGGAGCGAGACGATTAGG a          S  *  A  T  T  S  R  T  L  *  H  R  L  E  T  S  L  C  *  S  -
b             V  R  P  P  L  Q  E  L  C  S  T  A  Y  I  P  R  S  A  N  P  -
c               L  G  H  H  F  K  N  S  V  A  P  P  T  Y  L  A  L  L  I  L  -

AlwNI
                              |
           TGTTACCAGTGGCTGCTGCCAGTGGCGATAAGTCGTGTCTTACCGGGTTGGACTCAAGAC
    421    ------+---------+---------+---------+---------+---------+ 480
           ACAATGGTCACCGACGACGGTCACCGCTATTCAGCACAGAATGGCCCAACCTGAGTTCTG a          C  Y  Q  W  L  L  P  V  A  I  S  R  V  L  P  G  W  T  D  D  -
b             V  T  S  G  C  C  Q  W  R  *  V  V  S  Y  R  V  G  L  K  T  -
c               L  P  V  A  A  A  S  G  D  K  S  C  L  T  G  L  D  S  R  R  -

BsiHKAI
                                         ApaLI     |
                                            |      |
           GATAGTTACCGGATAAGGCGCAGCGGTCGGGCTGAACGGGGGGTTCGTGCACACAGCCCA
    481    ------+---------+---------+---------+---------+---------+ 540
           CTATCAATGGCCTATTCCGCGTCGCCAGCCCGACTTGCCCCCCAAGCACGTGTGTCGGGT a          D  S  Y  R  I  R  R  S  G  R  A  E  R  G  V  R  A  H  S  P  -
b             I  V  T  G  *  G  A  A  V  G  L  N  G  G  F  V  H  T  A  Q  -
c               *  L  P  D  K  A  Q  R  S  G  *  T  G  G  S  C  T  Q  P  S  -

GCTTGGAGCGAACGACCTACACCGAACTGAGATACCTACAGCGTGAGCTATGAGAAAGCG
    541    ------+---------+---------+---------+---------+---------+ 600
           CGAACCTCGCTTGCTGGATGTGGCTTGACTCTATGGATGTCGCACTCGATACTCTTTCGC a          A  W  S  E  R  P  T  P  N  *  D  T  Y  S  V  S  Y  E  K  A  -
b             L  G  A  N  D  L  H  R  T  E  I  P  T  A  *  A  M  R  K  R  -
c               L  E  R  T  T  Y  T  E  L  R  Y  L  Q  R  E  L  *  E  S  A  -

BclVI
                                   |
           CCACGCTTCCCGAAGGGAGAAAGGCGGACAGGTATCCGGTAAGCGGCAGGGTCGGAACAG
    601    ------+---------+---------+---------+---------+---------+ 660
           GGTGCGAAGGGCTTCCCTCTTTCCGCCTGTCCATAGGCCATTCGCCGTCCCAGCCTTGTC a          P  R  F  P  K  G  E  R  R  T  G  I  R  *  A  A  G  S  E  Q  -
b             H  A  S  R  R  E  K  G  G  Q  V  S  G  K  R  Q  G  R  N  R  -
c               T  L  P  E  G  R  K  A  D  R  Y  P  V  S  G  R  V  G  T  G  -

BssSI
                     |
           GAGAGCGCACGAGGGAGCTTCCAGGGGGAAACGCCTGGTATCTTTATAGTCCTGTCGGGT
    661    ------+---------+---------+---------+---------+---------+ 720
           CTCTCGCGTGCTCCCTCGAAGGTCCCCCTTTGCGGACCATAGAAATATCAGGACAGCCCA a          E  S  A  R  G  S  F  Q  G  G  E  T  P  G  I  F  I  V  L  S  G  -
b             R  A  H  E  G  A  S  R  G  K  R  L  V  S  L  *  S  C  R  V  -
```

Figure 7 (cont.)

```
c         E  R  T  R  E  L  P  G  G  N  A  W  Y  L  Y  S  P  V  G  F -
          TTCGCCACCTCTGACTTGAGCGTCGATTTTTGTGATGCTCGTCAGGGGGCGGAGCCTAT
     721  ----------+----------+----------+----------+----------+----------+ 780
          AAGCGGTGGAGACTGAACTCGCAGCTAAAAACACTACGAGCAGTCCCCCGCCTCGGATA a         F  A  T  S  D  L  S  V  D  F  C  D  A  R  Q  G  G  G  A  Y  -
b          S  P  P  L  T  *  A  S  I  F  V  M  L  V  R  G  A  E  P  M  -
c           R  H  L  *  L  E  R  R  F  L  *  C  S  S  G  G  R  S  L  W -
          GGAAAAACGCCAGCAACGCGGCCTTTTTACGGTTCCTGGCCTTTTGCTGGCCTTTTGCTC
     781  ----------+----------+----------+----------+----------+----------+ 840
          CCTTTTTGCGGTCGTTGCGCCGGAAAAATGCCAAGGACCGGAAAAACGACCGGAAAACGAG a         G  K  T  P  A  T  R  P  P  Y  G  S  W  P  F  A  G  L  L  L  -
b          E  K  R  Q  Q  R  G  L  F  T  V  P  G  L  L  L  A  F  C  S  -
c           K  N  A  S  N  A  A  F  L  R  F  L  A  F  C  W  P  F  A  H -
          ACATGTTCTTTCCTGCGTTATCCCCTGATTCTGTGGATAACCGTATTACCGCCTTTGAGT
     841  ----------+----------+----------+----------+----------+----------+ 900
          TGTACAAGAAAGGACGCAATAGGGGACTAAGACACCTATTGGCATAATGGCGGAAACTCA a         T  C  S  F  L  R  Y  P  L  I  L  W  I  T  V  L  P  P  L  S  -
b          H  V  L  S  C  V  I  P  *  F  C  G  *  P  Y  Y  R  L  *  V  -
c           M  F  F  P  A  L  S  P  D  S  V  D  N  R  I  T  A  F  E  * -
          GAGCTGATACCGCTCGCCGCAGCCGAACGACCGAGCGCAGCGAGTCAGTGAGCGAGGAAG
     901  ----------+----------+----------+----------+----------+----------+ 960
          CTCGACTATGGCGAGCGGCGTCGGCTTGCTGGCTCGCGTCGCTCAGTCACTCGCTCCTTC a         S  L  I  P  L  A  A  A  E  R  P  S  A  A  S  Q  *  A  R  K  -
b          S  *  Y  R  S  P  Q  P  N  D  R  A  Q  R  V  S  E  R  G  S  -
c           A  D  T  A  R  R  S  R  T  T  E  R  S  E  S  V  S  E  E  A -
          CGGAAGAGCGCCCAATACGCAAACCGCCTCTCCCCGCGCGTTGGCCGATTCATTAATGCA
     961  ----------+----------+----------+----------+----------+----------+ 1020
          GCCTTCTCGCGGGTTATGCGTTTGGCGGAGAGGGGCGCGCAACCGGCTAAGTAATTACGT a         R  K  S  A  Q  Y  A  N  R  L  S  P  R  V  G  R  F  I  N  A  -
b          G  R  A  P  N  T  Q  T  A  S  P  R  A  L  A  D  S  L  M  Q  -
c           E  E  R  P  I  R  K  P  P  L  P  A  R  W  P  I  H  *  C  R -
          EagI
          NotI
            |
          GagcGGCCGCCTCAAGGCGCACTCCCGTTCTGGATAATGTTTTTTGCGCCGACATCATAA
    1021  ----------+----------+----------+----------+----------+----------+ 1080
          CtcgCCGGCGGAGTTCCGCGTGAGGGCAAGACCTATTACAAAAAACGCGGCTGTAGTATT a         E  R  P  P  Q  G  A  L  P  F  W  I  M  F  F  A  P  T  S  *  -
b          S  G  R  L  K  A  H  S  R  S  G  *  C  F  L  R  R  H  H  N  -
c           A  A  A  S  R  R  T  P  V  L  D  N  V  F  C  A  D  I  I  T -

HpaI
                                                       |
          CGGTTCTGGCAAATATTCTGAAATGAGCTGTTGACAATTAATCATCGAACTAGTTAACTA
```

Figure 7 (cont.)

```
1081 ----------+----------+----------+----------+----------+----------+ 1140
     GCCAAGACCGTTTATAAGACTTTACTCGACAACTGTTAATTAGTAGCTTGATCAATTGAT
``` a    R F W Q I F * N E L L T I N H R T S * L -
b      G S G K Y S E M S C * Q L I I E L V N * -
c        V L A N I L K * A V D N * S S N * L T S -

HindIII
                                                  |
     GTACGCAAGTTCACGTAAAAAGGGTATCGACAATGAAAGCAATTTTCGTACTGAAAGCTT
1141 ----------+----------+----------+----------+----------+----------+ 1200
     CATGCGTTCAAGTGCATTTTTCCCATAGCTGTTACTTTCGTTAAAAGCATGACTTTCgAA a    V R K F T * K G Y R Q * K Q F S Y * K L -
b      Y A S S R K K G I D N E S N F R T E S F -
c        T Q V H V K R V S T M K A I F V L K A S -

CtAATGATGATAAGTTATATAaGGCAGATTCTAGACCTCCTGATGAAATAAAGCAGTCAG
1201 ----------+----------+----------+----------+----------+----------+ 1260
     gaTTACTACTATTCAATATAttCCGTCTAAGATCTGGAGGACTACTTTATTTCGTCAGTC a    L M M I S Y I R Q I L D L L M K * S S Q -
b     * * * * V I * G R F * T S * * N K A V R -
c        N D D K L Y K A D S R P P D E I K Q S G -

ScaI
                                TatI
                                  |
     GTGGTCTTATGCCAAGAGGACAGAGTGAGTACTTTGACCGAGGTACTCAAATGAATATCA
1261 ----------+----------+----------+----------+----------+----------+ 1320
     CACCAGAATACGGTTCTCCTGTCTCACTCATGAAACTGGCTCCATGAGTTTACTTATAGT a    V V L C Q E D R V S T L T E V L K * I S -
b      W S Y A K R T E * V L * P R Y S N E Y Q -
c        G L M P R G Q S E Y F D R G T Q M N I N -

BclI
       |
     ACCTTTATGATCATGCAAGAGGAACTCAGACGGGATTTGTTAGGCACGATGATGGATATG
1321 ----------+----------+----------+----------+----------+----------+ 1380
     TGGAAATACTAGTACGTTCTCCTTGAGTCTGCCCTAAACAATCCGTGCTACTACCTATAC a    T F M I M Q E E L R R D L L G T M M D M -
b      P L * S C K R N S D G I C * A R * W I C -
c        L Y D H A R G T Q T G F V R H D D G Y V -

DraIII
                              |
     TTTCCACGTCAATTAGTTTGAGAAGTGCCCACTTAGTGGGTCAAACTATATTGTCTGGTC
1381 ----------+----------+----------+----------+----------+----------+ 1440
     AAAGGTGGAGTTAATCAAACTCTTCACGGGTGAATCACCCAGTTTGATATAACAGACCAG a    F P P Q L V * E V P T * W V K L Y C L V -
b      F H L N * P E K C P L S G S N Y I V W S -
c        S T S I S L R S A H L V G Q T I L S G H -
           BsgI
             |
```

Figure 7 (cont.)

```
        ATTCTACTTATTATATATATGTTATAGCCACTGCACCCAACATGTTTAACGTTAATGATG
   1441 ------------+----------+----------+----------+----------+ 1500
        TAAGATGAATAATATATATACAATATCGGTGACGTGGGTTGTACAAATTGCAATTACTAC a     I  L  L  I  I  Y  M  L  *  P  L  H  P  T  C  L  T  L  M  M   -
   b      Y  L  L  Y  I  C  Y  S  H  C  T  Q  H  V  *  R  *  *  C   -
   c       S  T  Y  Y  I  Y  V  I  A  T  A  P. N  M  F  N  V  N  D  V -

TATTAGGGGCATACAGTCCTCATCCAGATGAACAAGAAGTTTCTGCTTTAGGTGGGATTC
   1501 ------------+----------+----------+----------+----------+ 1560
        ATAATCCCCGTATGTCAGGAGTAGGTCTACTTGTTCTTCAAAGACGAAATCCACCCTAAG a     Y  *  G  H  T  V  L  I  Q  M  N  K  K  F  L  L  *  V  G  F   -
   b      I  R  G  I  Q  S  S  S  R  *  T  R  S  F  C  F  R  W  D  S  -
   c       L  G  A  Y  S  P  H  P  D  E  Q  E  V  S  A  L  G  G  I  P -

BstXI
                  |
        CATACTCCCAAATATATGGATGGTATCGAGTTCATTTTGGGGTGCTTGATGAACAATTAC
   1561 ------------+----------+----------+----------+----------+ 1620
        GTATGAGGGTTTATATACCTACCATAGCTCAAGTAAAACCCCACGAACTACTTGTTAATG a     H  T  P  K  Y  M  D  G  I  E  F  I  L  G  C  L  M  N  N  Y   -
   b      I  L  P  N  I  W  M  V  S  S  S  F  W  G  A  *  *  T  I  T  -
   c       Y  S  Q  I  Y  G  W  Y  R  V  H  F  G  V  L  D  E  Q  L  H -

BpmI
                                            |
        ATCGTAATAGGGGCTACAGAGATAGATATTACAGTAACTTAGATATTGCTCCAGCAGCAG
   1621 ------------+----------+----------+----------+----------+ 1680
        TAGCATTATCCCCGATGTCTCTATCTATAATGTCATTGAATCTATAACGAGGTCGTCGTC a     I  V  I  G  A  T  E  I  D  I  T  V  T  *  I  L  L  Q  Q  Q   -
   b      S  *  *  G  L  Q  R  *  I  L  Q  *  L  R  Y  C  S  S  R   -
   c       R  N  R  G  Y  R  D  R  Y  Y  S  N  L  D  I  A  P  A  A  D -

ATGGTTATGGATTGGCAGGTTTCCCTCCGGAGCATAGAGCTTGGAGGGAAGAGCCGTGGA
   1681 ------------+----------+----------+----------+----------+ 1740
        TACCAATACCTAACCGTCCAAAGGGAGGCCTCGTATCTCGAACCTCCCTTCTCGGCACCT a     M  V  M  D  W  Q  V  S  L  R  S  I  E  L  G  G  K  S  R  G   -
   b      W  L  W  I  G  R  F  P  S  G  A  *  S  L  E  G  R  A  V  D  -
   c       G  Y  G  L  A  G  F  P  P  E  H  R  A  W  R  E  E  P  W  I -

RleAI                              BamHI           EbaI
                |                                  |              |
        TTCATCATGCACCGCCGGGTTGTGGGAATGCTCCAAGATCATCGggatccgggaagacac
   1741 ------------+----------+----------+----------+----------+ 1800
        AAGTAGTACGTGGCGGCCCAACACCCTTACGAGGTTCTAGTAGCcctaggccctctgtg a     F  I  M  H  R  R  V  V  G  M  L  Q  D  H  R  D  P  G  R  H   -
   b      S  S  C  T  A  G  L  W  E  C  S  K  I  I  G  I  R  E  D  T  -
   c       H  H  A  P  P  G  C  G  N  A  P  R  S  S  G  S  G  K  T  P -

BglII
          |
        ccgagATCTCCCAGGCTGTTCACGCTGCTCACGCTGAAATCAACGAAGCTGGTCGTGCCC
   1801 ------------+----------+----------+----------+----------+ 1860
```

Figure 7 (cont.)

```
       ggctcTAGAGGGTCCGACAAGTGCGACGAGTGCGACTTTAGTTGCTTCGACCAGCACGGg
a      P R S P R L P T L L T L K S T K L V V P  -
b       R D L P G C S R C S R * N Q R S W S C P -
c        E I S Q A V H A A H A E I N E A G R A P -

BglI
         |
       ccgagGCTGATGCGCAACAAAATAACTTCAACAAAGATCAACAAAGCGCCTTCTATGAAA
  1861 --------+---------+---------+---------+---------+---------+ 1920
       ggctcCGACTACGCGTTGTTTTATTGAAGTTGTTTCTAGTTGTTTCGCGGAAGATACTTT a       P R L M R N K I T S T K I N K A P S M K  -
b         R G * C A T K * L Q Q R S T K R L L * N -
c          E A D A Q Q N N F N K D Q Q S A F Y E I -

TCTTGAACATGCCTAACTTAAACGAAGCGCAACGTAACGGCTTCATTCAAAGTCTTAAAG
  1921 --------+---------+---------+---------+---------+---------+ 1980
       AGAACTTGTACGGATTGAATTTGCTTCGCGTTGCATTGCCGAAGTAAGTTTCAGAATTTC a      S * T C L T * T K R N V T A S F K V L K  -
b       L E H A * L K R S A T * R L H S K S * R -
c        L N M P N L N E A Q R N G F I Q S L K D -

ACGACCCAAGCCAAAGCACTAACGTTTTAGGTGAAGCTAAAAAATTAAACGAATCTCAAG
  1981 --------+---------+---------+---------+---------+---------+ 2040
       TGCTGGGTTCGGTTTCGTGATTGCAAAATCCACTTCGATTTTTTAATTTGCTTAGAGTTC a      T T Q A K A L T F * V K L K N * T N L K  -
b       R P K P K H * R F R * S * K I K R I S S -
c        D P S Q S T N V L G E A K K L N E S Q A -

CACCCAAAcccgagGCTGATGCGCAACAAAATAACTTCAACAAAGATCAACAAAGCGCCT
  2041 --------+---------+---------+---------+---------+---------+ 2100
       GTGGGTTTgggctcCGACTACGCGTTGTTTTATTGAAGTTGTTTCTAGTTGTTTCGCGGA a      H P N P R L M R N K I T S T K I N K A P  -
b       T Q T R G * C A T K * L Q Q R S T K R L -
c        P K P E A D A Q Q N N F N K D Q Q S A F -

TCTATGAAATCTTGAACATGCCTAACTTAAACGAAGCGCAACGTAACGGCTTCATTCAAA
  2101 --------+---------+---------+---------+---------+---------+ 2160
       AGATACTTTAGAACTTGTACGGATTGAATTTGCTTCGCGTTGCATTGCCGAAGTAAGTTT a      S M K S * T C L T * T K R N V T A S F K  -
b       L * N L E H A * L K R S A T * R L H S K -
c        Y E I L N M P N L N E A Q R N G F I Q S -

GTCTTAAAGACGACCCAAGCCAAAGCACTAACGTTTTAGGTGAAGCTAAAAAATTAAACG
  2161 --------+---------+---------+---------+---------+---------+ 2220
       CAGAATTTCTGCTGGGTTCGGTTTCGTGATTGCAAAATCCACTTCGATTTTTTAATTTGC a      V L K T T Q A K A L T F * V K L K N * T  -
b       S * R R P K P K H * R F R * S * K I K R -
c        L K D D P S Q S T N V L G E A K K L N E -

AATCTCAAGCACCCAAAcccgaggtagcaggtcagaattAGCTTGCTGATTGATTGACCG
  2221 --------+---------+---------+---------+---------+---------+ 2280
```

Figure 7 (cont.)

```
             TTAGAGTTCGTGGGTTTgggctccatcgtccagtcttaaTCGAACGACTAACTAACTGGC
a            N  L  K  H  P  N  P  R  *  Q  V  R  I  S  L  L  I  D  *  P  -
b              I  S  S  T  Q  T  R  G  S  R  S  E  L  A  C  *  L  I  D  R -
c                S  Q  A  P  K  P  E  V  A  G  Q  N  *  L  A  D  *  L  T  G -

XmnI
                           |
       GATCGATCCGGCTCTAGAATTAATTCACCTCGAAAGCAAGCTGATAAACCGATACAATTA
  2281 ------+---------+---------+---------+---------+---------+ 2340
       CTAGCTAGGCCGAGATCTTAATTAAGTGGAGCTTTCGTTCGACTATTTGGCTATGTTAAT a            D  R  S  G  S  R  I  N  S  P  R  K  Q  A  D  K  P  I  Q  L  -
b              I  D  P  A  L  E  L  I  H  L  E  S  K  L  I  N  R  Y  N  * -
c                S  I  R  L  *  N  *  F  T  S  K  A  S  *  *  T  D  T  I  K -

AAGGCTCCTTTTTGGAGCCTTTTTTTTTGGAGATTTTCAACGTGAAAAAATTATTATTCGC
  2341 ------+---------+---------+---------+---------+---------+ 2400
       TTCCGAGGAAAAACCTCGGAAAAAAAAACCTCTAAAAGTTGCACTTTTTTAATAATAAGCG a            K  A  P  F  G  A  F  F  F  G  D  F  Q  R  E  K  I  I  I  R  -
b              R  L  L  L  E  P  F  F  L  E  I  F  N  V  K  K  L  L  F  A -
c                G  S  F  W  S  L  F  F  W  R  F  S  T  *  K  N  Y  Y  S  Q -

AATTCAAGCTAATTCACCTAGAAAAGCAAGCTGATAAACCGATACAATTAAAGGCTCCTTT
  2401 ------+---------+---------+---------+---------+---------+ 2460
       TTAAGTTCGATTAAGTGGATCTTTTCGTTCGACTATTTGGCTATGTTAATTTCCGAGGAAA a            N  S  S  *  F  T  *  K  A  S  *  *  T  D  T  I  K  G  S  F  -
b              I  Q  A  N  S  P  R  K  Q  A  D  K  P  I  Q  L  K  A  P  F -
c                F  K  L  I  H  L  E  S  K  L  I  N  R  Y  N  *  R  L  L  L -

TGGAGCCTTTTTTTTTGGAGATTTTCAACGTGAAAAAATTATTATTCGCAATTCAAGCTC
  2461 ------+---------+---------+---------+---------+---------+ 2520
       ACCTCGGAAAAAAAAAACCTCTAAAAGTTGCACTTTTTTAATAATAAGCGTTAAGTTCGAG a            W  S  L  F  F  W  R  F  S  T  *  K  N  Y  Y  S  Q  F  K  L  -
b              G  A  F  F  F  G  D  F  Q  R  E  K  I  I  I  R  N  S  S  S -
c                E  P  F  F  L  E  I  F  N  V  K  K  L  L  F  A  I  Q  A  L -

TGCCTCGCGCGTTTCGGTGATGACGGTGAAAACCTCTGACACATGCAGCTCCCGGAGACG
  2521 ------+---------+---------+---------+---------+---------+ 2580
       ACGGAGCGCGCAAAGCCACTACTGCCACTTTTGGAGACTGTGTACGTCGAGGGCCTCTGC a            C  L  A  R  F  G  D  D  G  E  N  L  *  H  M  Q  L  P  E  T  -
b              A  S  R  V  S  V  M  T  V  K  T  S  D  T  C  S  S  R  R  R -
c                P  R  A  F  R  *  *  R  *  K  P  L  T  H  A  A  P  G  D  G -

GTCACAGCTTGTCTGTAAGCGGATGCCGGGAGCAGACAAGCCCGTCAGGGCGCGTCAGCG
  2581 ------+---------+---------+---------+---------+---------+ 2640
       CAGTGTCGAACAGACATTCGCCTACGGCCCTCGTCTGTTCGGGCAGTCCCGCGCAGTCGC a            V  T  A  C  L  *  A  D  A  G  S  R  Q  A  R  Q  G  A  S  A  -
b              S  Q  L  V  C  K  R  M  P  G  A  D  K  P  V  R  A  R  Q  R -
c                H  S  L  S  V  S  G  C  R  E  Q  T  S  P  S  G  R  V  S  G -

BsbI                        BfiI    Tth111I
                                              |
```

Figure 7 (cont.)

```
           |                              |           |
           GGTGTTGGCGGGTGTCGGGGCGCAGCCATGACCCAGTCACGTAGCGATAGCGGAGTGTAT
      2641 ------------+----------+----------+----------+----------+----------+ 2700
           CCACAACCGCCCACAGCCCCGCGTCGGTACTGGGTCAGTGCATCGCTATCGCCTCACATA
``` a   G V G G C R G A A M T Q S R S D S G V Y -
b     V L A G V G A Q P * P S H V A I A E C M -
c       C W R V S G R S H D P V T * R * R S V C -

```
                        BsrDI
                          |
           GTGTCTCAAAATCTCTGATGTTACATTGCACAAGATAAAAATATATCATCATGAACAATA
      2701 ------------+----------+----------+----------+----------+----------+ 2760
           CACAGAGTTTTAGAGACTACAATGTAACGTGTTCTATTTTTATATAGTAGTACTTGTTAT
``` a   V S Q N L * C Y I A Q D K N I S S * T I -
b     C L K I S D V T L H K I K I Y H E Q * -
c       V S K S L M L H C T R * K Y I I M N N K -

```
           AAACTGTCTGCTTACATAAACAGTAATACAAGGGGTGTTATGAGCCATATTCAACGGGAA
      2761 ------------+----------+----------+----------+----------+----------+ 2820
           TTTGACAGACGAATGTATTTGTCATTATGTTCCCCACAATACTCGGTATAAGTTGCCCTT
``` a   K L S A Y I N S N T R G V M S H I Q R E -
b     N C L L T * T V I Q G V L * A I F N G K -
c       T V C L H K Q * Y K G C Y E P Y S T G N -

```
                XhoI
                  |
           ACGTCTTGCTCGAGGCCGCGATTAAAATTCCAACATGGATGCTGATTTATATGGGTATAAA
      2821 ------------+----------+----------+----------+----------+----------+ 2880
           TGCAGAACGAGCTCCGGCGCTAATTTAAGGTTGTACCTACGACTAAATATACCCATATTT
``` a   T S C S R P R L N S N M D A D L Y G Y K -
b     R L A R G R D * I P T W M L I Y M G I N -
c       V L L E A A I K F Q H G C * F I W V * M -

```
               NruI
           BanII |
              | |
           TGGGCTCGCGATAATGTCGGGCAATCAGGTGCGACAATCTATCGATTGTATGGGAAGCCC
      2881 ------------+----------+----------+----------+----------+----------+ 2940
           ACCCGAGCGCTATTACAGCCCGTTAGTCCACGCTGTTAGATAGCTAACATACCCTTCGGG
``` a   W A R D N V G Q S G A T I Y R L Y G K P -
b     G L A I M S G N Q V R Q S I D C M G S P -
c       G S R * C R A I R C D N L S I V W E A R -

```
           GATGCGCCAGAGTTGTTTCTGAAACATGGCAAAGGTAGCGTTGCCAATGATGTTACAGAT
      2941 ------------+----------+----------+----------+----------+----------+ 3000
           CTACGCGGTCTCAACAAAGACTTTGTACCGTTTCCATCGCAACGGTTACTACAATGTCTA
``` a   D A P E L F L K H G K G S V A N D V T D -
b     M R Q S C F * N M A K V A L P M M L Q M -
c       C A R V V S E T W Q R * R C Q * C Y R * -

```
           GAGATGGTCAGACTAAACTGGCTGACGGAATTTATGCCTCTTCCGACCATCAAGCATTTT
      3001 ------------+----------+----------+----------+----------+----------+ 3060
```

Figure 7 (cont.)

```
        CTCTACCAGTCTGATTTGACCGACTGCCTTAAATACGGAGAAGGCTGGTAGTTCGTAAAA
a        E  M  V  R  L  N  W  L  T  E  F  M  P  L  P  T  I  K  R  F   -
b         R  W  S  D  *  T  G  *  R  N  L  C  L  F  R  P  S  S  I  L  -
c          D  G  Q  T  K  L  A  D  G  I  Y  A  S  S  D  H  Q  A  F  Y  -

, SmaI
        ATCCGTACTCCTGATGATGCATGGTTACTCACCACTGCGATCCCCGGGAAAACAGCATTC
3061    ------+---------+---------+---------+---------+---------+  3120
        TAGGCATGAGGACTACTACGTACCAATGAGTGGTGACGCTAGGGGCCCTTTTGTCGTAAG
a        I  R  T  P  D  D  A  W  L  L  T  T  A  I  P  G  K  T  A  F   -
b         S  V  L  L  M  M  H  G  Y  S  P  L  R  S  P  G  K  Q  H  S  -
c          P  Y  S  *  *  C  M  V  T  H  H  C  D  P  R  E  N  S  I  P -

EcoNI
        CAGGTATTAGAAGAATATCCTGATTCAGGTGAAAATATTGTTGATGCGCTGGCAGTGTTC
3121    ------+---------+---------+---------+---------+---------+  3180
        GTCCATAATCTTCTTATAGGACTAAGTCCACTTTTATAACAACTACGCGACCGTCACAAG
a        Q  V  L  E  E  Y  P  D  S  G  E  N  I  V  D  A  L  A  V  F  -
b         R  Y  *  K  N  I  L  I  Q  V  K  I  L  L  M  R  W  Q  C  S  -
c          G  I  R  R  I  S  *  F  R  *  K  Y  C  *  C  A  G  S  V  P -

PvuI
        BsrFI                                       SgfI
        CTGCGCCGGTTGCATTCGATTCCTGTTTGTAATTGTCCTTTTAACAGCGATCGCGTATTT
3181    ------+---------+---------+---------+---------+---------+  3240
        GACGCGGCCAACGTAAGCTAAGGACAAACATTAACAGGAAAATTGTCGCTAGCGCATAAA
a        L  R  R  L  H  S  I  P  V  C  N  C  P  F  N  S  D  R  V  F  -
b         C  A  G  C  I  R  F  L  F  V  I  V  L  L  T  A  I  A  Y  F -
c          A  P  V  A  F  D  S  C  L  *  L  S  F  *  Q  R  S  R  I  S -

Bpu10I
        CGTCTCGCTCAGGCGCAATCACGAATGAATAACGGTTTGGTTGATGCGAGTGATTTTGAG
3241    ------+---------+---------+---------+---------+---------+  3300
        GCAGAGCGAGTCCGCGTTAGTGCTTACTTATTGCCAAACCAACTACGCTCACTAAAACTC
a        R  L  A  Q  A  Q  S  R  M  N  N  G  L  V  D  A  S  D  F  E  -
b         V  S  L  R  R  N  H  E  *  I  T  V  W  L  M  R  V  I  L  R -
c          S  R  S  G  A  I  T  N  E  *  R  F  G  *  C  E  *  F  *  D -

ACGAGCGTAATGGCTGGCCTGTTGAACAAGTCTGGAAAGAAATGCATAAACTTTTGCCAT
3301    ------+---------+---------+---------+---------+---------+  3360
        TGCTCGCATTACCGACCGGACAACTTGTTCAGACCTTTCTTTACGTATTTGAAAACGGTA
a        T  S  V  M  A  G  L  L  N  K  S  G  K  K  C  I  N  F  C  H  -
b         R  A  *  W  L  A  C  *  T  S  L  E  R  N  A  *  T  F  A  I -
c          E  R  N  G  W  P  V  E  Q  V  W  K  E  M  H  K  L  L  P  F -

TCTCACCGGATTCAGTCGTCACTCATGGTGATTTCTCACTTGATAACCTTATTTTTGACG
3361    ------+---------+---------+---------+---------+---------+  3420
        AGAGTGGCCTAAGTCAGCAGTGAGTACCACTAAAGAGTGAACTATTGGAATAAAAACTGC
```

Figure 7 (cont.)

```
a        S  H  R  I  Q  S  S  L  M  V  I  S  H  L  I  T  L  F  L  T  -
b          L  T  G  F  S  R  H  S  W  *  P  L  T  *  *  P  Y  F  *  R  -
c            S  P  D  S  V  V  T  H  G  D  P  S  L  D  N  L  I  F  D  E -
        AGGGGAAATTAATAGGTTGTATTGATGTTGGACGAGTCGGAATCGCAGACCGATACCAGG
   3421 ------------+---------+---------+---------+---------+---------+ 3480
        TCCCCTTTAATTATCCAACATAACTACAACCTGCTCAGCCTTAGCGTCTGGCTATGGTCC a        R  G  N  *  *  V  V  L  M  L  D  E  S  E  S  Q  T  D  T  R  -
b          G  E  I  N  R  L  Y  *  C  W  T  S  R  N  R  R  P  I  P  G  -
c            G  K  L  I  G  C  I  D  V  G  R  V  G  I  A  D  R  Y  Q  D -
        ATCTTGCCATCCTATGGAACTGCCTCGGTGAGTTTTCTCCTTCATTACAGAAACGGCTTT
   3481 ------------+---------+---------+---------+---------+---------+ 3540
        TAGAACGGTAGGATACCTTGACGGAGCCACTCAAAAGAGGAAGTAATGTCTTTGCCGAAA a        I  L  P  S  Y  G  T  A  S  V  S  F  L  L  H  Y  R  N  G  F  -
b          S  C  H  P  M  E  L  P  R  *  V  P  S  F  I  T  E  T  A  F  -
c            L  A  I  L  W  N  C  L  G  E  F  S  P  S  L  Q  K  R  L  F -
        TTCAAAAATATGGTATTGATAATCCTGATATGAATAAATTGCAGTTTCATTTGATGCTCG
   3541 ------------+---------+---------+---------+---------+---------+ 3600
        AAGTTTTTATACCATAACTATTAGGACTATACTTATTTAACGTCAAAGTAAACTACGAGC a        F  K  N  M  V  L  I  I  L  I  *  I  N  C  S  F  I  *  C  S  -
b          S  K  I  W  Y  *  *  S  *  Y  E  *  I  A  V  S  F  D  A  R  -
c            Q  K  Y  G  I  D  N  P  D  M  N  K  L  Q  F  H  L  M  L  D -
        ATGAGTTTTTCTAATCAGAATTGGTTAATTGGTTGTAACACTGGCAGAGCATTACGCTGA
   3601 ------------+---------+---------+---------+---------+---------+ 3660
        TACTCAAAAAGATTAGTCTTAACCAATTAACCAACATTGTGACCGTCTCGTAATGCGACT a        M  S  F  S  N  Q  N  W  L  I  G  C  N  T  G  R  A  L  R  *  -
b          *  V  F  L  I  R  I  G  *  L  V  V  T  L  A  E  H  Y  A  D  -
c            E  F  F  *  S  E  L  V  N  W  L  *  H  W  Q  S  I  T  L  T -
                                    BsmFI
                                      |
        CTTGACGGGACGGCGGCTTTGTTGAATAAATCGAACTTTTGCTGAGTTGAAGGATCAGAT
   3661 ------------+---------+---------+---------+---------+---------+ 3720
        GAACTGCCCTGCCGCCGAAACAACTTATTTAGCTTGAAAACGACTCAACTTCCTAGTCTA a        L  D  G  T  A  A  L  L  N  K  S  N  F  C  *  V  E  G  S  D  -
b          L  T  G  R  R  L  C  *  I  N  R  T  P  A  E  L  K  D  Q  I  -
c            *  R  D  G  G  F  V  E  *  I  E  L  L  S  *  R  I  R  S   -
        CACGCATCTTCCCGACAACGCAGACCGTTCCGTGGCAAAGCAAAAGTTCAAAATCACCAA
   3721 ------------+---------+---------+---------+---------+---------+ 3780
        GTGCGTAGAAGGGCTGTTGCGTCTGGCAAGGCACCGTTTCGTTTTCAAGTTTTAGTGGTT a        H  A  S  S  R  Q  R  R  P  F  R  G  K  A  K  V  Q  N  H  Q  -
b          T  H  L  P  D  N  A  D  R  S  V  A  K  Q  K  F  K  I  T  N  -
c            R  I  F  P  T  T  Q  T  V  P  W  Q  S  K  S  S  K  S  P  T -
        AvaII
        Sau96I
```

Figure 7 (cont.)

```
         CTGGTCCGgatcGATCCG
3781  ------------+--------  3798
         GACCAGGCctagCTAGGC a        L  V  R  I  D  P    -
b           W  S  G  S  I    -
c              G  P  D  R  S -
```

Enzymes that do cut and were not excluded:

| AlwNI | ApaLI | AvaII | BamHI | BanII | BbsI | BciVI | BclI |
|---|---|---|---|---|---|---|---|
| BfiI | BglI | BglII | BpmI | Bpu10I | BsbI | BsgI | BsiHKAI |
| BsmFI | BsrDI | BsrFI | BssSI | BstXI | DraIII | FagI | Eco57I |
| EcoNI | HgiEII | HindIII | HpaI | NotI | NruI | PvuI | RleAI |
| Sau96I | ScaI | SgfI | SmaI | TatI | Tth111I | XhoI | XmnI |

Enzymes that do not cut:

| AatII | AccI | AflII | AhdI | ApaI | AscI | AvrII | BaeI |
|---|---|---|---|---|---|---|---|
| BanI | BplI | Bpu1102I | BsaI | BsaBI | BsaHI | BseRI | BspGI |
| BsrGI | BssHII | BstAPI | BstEII | BstZ17I | Bsu36I | DrdII | Eco47III |
| Eco0109I | EcoRI | EcoRV | FseI | KpnI | MluI | MscI | MunI |
| NarI | NcoI | NdeI | NgoAIV | NheI | NspV | PacI | Pfl1108I |
| PinAI | PmeI | PmlI | PshAI | PspSII | PstI | PvuII | RsrII |
| SacI | SacII | SalI | SanDI | SbfI | SexAI | SfiI | SgrAI |
| SmiI | SnaBI | SphI | SrfI | Sse8647I | StuI | StyI | SunI |
| UbaDI | UbaEI | XcmI | | | | | |

Enzymes excluded; MinCuts: 1 MaxCuts: 1

| AceIII | AciI | AflIII | AluI | AlwI | ApoI | AvaI | BbvI |
|---|---|---|---|---|---|---|---|
| BccI | Bce83I | BcefI | BcgI | BcgI | BfaI | BmgI | BsaAI |
| BsaJI | BsaWI | BsaXI | BscGI | BseMII | BsiEI | BslI | BsmI |
| BsmAI | BsmBI | Bsp24I | Bsp24I | Bsp1286I | BspEI | BspLU11I | BspMI |
| BsrI | BsrBI | Bst4CI | BstDSI | BstYI | Cac8I | CjeI | CjeI |
| CjePI | CjePI | ClaI | CviJI | CviRI | DdeI | DpnI | DraI |
| DrdI | EaeI | EarI | EciI | EcoRII | FauI | Fnu4HI | FokI |
| FspI | GdiII | HaeI | HaeII | HaeIII | HgaI | HhaI | Hin4I |
| HincII | HinfI | HphI | MaeIII | MboII | MmeI | MnlI | MseI |
| MslI | MspI | MspAI | MwoI | NciI | NlaIII | NlaIV | NsiI |
| NspI | PflMI | PleI | Psp1406I | RcaI | RsaI | SapI | Sau3AI |
| ScrFI | SfaNI | SfcI | SimI | SmlI | SpeI | SspI | TaiI |
| TaqI | TaqII | TaqII | TauI | TfiI | ThaI | TseI | Tsp45I |
| Tsp509I | TspRI | Tth111II | VspI | XbaI | | | |

Figure 8

CTA1DD
DNA and amino acid sequence

| | |
|---|---|
| atg aaa gca att ttc gta ctg aaa gct tct aat gat gat aag tta tat<br>Met Lys Ala Ile Phe Val Leu Lys Ala Ser Asn Asp Asp Lys Leu Tyr<br>1     5         10         15 | 48 |
| cgg gca gat tct aga cct cct gat gaa ata aag cag tca ggt ggt ctt<br>Arg Ala Asp Ser Arg Pro Pro Asp Glu Ile Lys Gln Ser Gly Gly Leu<br>      20         25         30 | 96 |
| atg cca aga gga cag agt gag tac ttt gac cga ggt act caa atg aat<br>Met Pro Arg Gly Gln Ser Glu Tyr Phe Asp Arg Gly Thr Gln Met Asn<br>      35         40         45 | 144 |
| atc aac ctt tat gat cat gca aga gga act cag acg gga ttt gtt agg<br>Ile Asn Leu Tyr Asp His Ala Arg Gly Thr Gln Thr Gly Phe Val Arg<br>      50         55         60 | 192 |
| cac gat gat gga tat gtt tcc acc tca att agt ttg aga agt gcc cac<br>His Asp Asp Gly Tyr Val Ser Thr Ser Ile Ser Leu Arg Ser Ala His<br>65         70         75         80 | 240 |
| tta gtg ggt caa act ata ttg tct ggt cat tct act tat tat ata tat<br>Leu Val Gly Gln Thr Ile Leu Ser Gly His Ser Thr Tyr Tyr Ile Tyr<br>      85         90         95 | 288 |
| gtt ata gcc act gca ccc aac atg ttt aac gtt aat gat gta tta ggg<br>Val Ile Ala Thr Ala Pro Asn Met Phe Asn Val Asn Asp Val Leu Gly<br>      100      105      110 | 336 |
| gca tac agt cct cat cca gat gaa caa gaa gtt tct gct tta ggt ggg<br>Ala Tyr Ser Pro His Pro Asp Glu Gln Glu Val Ser Ala Leu Gly Gly<br>      115      120      125 | 384 |
| att cca tac tcc caa ata tat gga tgg tat cga gtt cat ttt ggg gtg<br>Ile Pro Tyr Ser Gln Ile Tyr Gly Trp Tyr Arg Val His Phe Gly Val<br>      130      135      140 | 432 |
| ctt gat gaa caa tta cat cgt aat agg ggc tac aga gat aga tat tac<br>Leu Asp Glu Gln Leu His Arg Asn Arg Gly Tyr Arg Asp Arg Tyr Tyr<br>145     150      155      160 | 480 |
| agt aac tta gat att gct cca gca gca gat ggt tat gga ttg gca ggt<br>Ser Asn Leu Asp Ile Ala Pro Ala Ala Asp Gly Tyr Gly Leu Ala Gly<br>      165      170      175 | 528 |
| ttc cct ccg gag cat aga gct tgg agg gaa gag ccg tgg att cat cat<br>Phe Pro Pro Glu His Arg Ala Trp Arg Glu Glu Pro Trp Ile His His<br>      180      185      190 | 576 |
| gca ccg ccg ggt tgt ggg aat gct cca aga tca tcg gga tcc ggg aag<br>Ala Pro Pro Gly Cys Gly Asn Ala Pro Arg Ser Ser Gly Ser Gly Lys<br>      195      200      205 | 624 |

Figure 8 (cont.)

```
aca ccc gag gct gat gcg caa caa aat aac ttc aac aaa gat caa caa        672
Thr Pro Glu Ala Asp Ala Gln Gln Asn Asn Phe Asn Lys Asp Gln Gln
    210             215             220 agc gcc ttc tat gaa atc ttg aac atg cct aac tta aac gaa gcg caa        720
Ser Ala Phe Tyr Glu Ile Leu Asn Met Pro Asn Leu Asn Glu Ala Gln
    225             230             235             240 cgt aac ggc ttc att caa agt ctt aaa gac gac cca agc caa agc act        768
Arg Asn Gly Phe Ile Gln Ser Leu Lys Asp Asp Pro Ser Gln Ser Thr
        245             250             255 aac gtt tta ggt gaa gct aaa aaa tta aac gaa tct caa gca ccc aaa        816
Asn Val Leu Gly Glu Ala Lys Lys Leu Asn Glu Ser Gln Ala Pro Lys
        260             265             270 ccc gag gct gat gcg caa caa aat aac ttc aac aaa gat caa caa agc        864
Pro Glu Ala Asp Ala Gln Gln Asn Asn Phe Asn Lys Asp Gln Gln Ser
        275             280             285 gcc ttc tat gaa atc ttg aac atg cct aac tta aac gaa gcg caa cgt        912
Ala Phe Tyr Glu Ile Leu Asn Met Pro Asn Leu Asn Glu Ala Gln Arg
    290             295             300 aac ggc ttc att caa agt ctt aaa gac gac cca agc caa agc act aac        960
Asn Gly Phe Ile Gln Ser Leu Lys Asp Asp Pro Ser Gln Ser Thr Asn
305             310             315             320 gtt tta ggt gaa gct aaa aaa tta aac gaa tct caa gca ccc aaa ccc       1008
Val Leu Gly Glu Ala Lys Lys Leu Asn Glu Ser Gln Ala Pro Lys Pro
        325             330             335 gag gta gca ggt cag aat tag                                           1029
Glu Val Ala Gly Gln Asn
    340
```

IMMUNOGENIC COMPLEX

The present invention relates to new immunogenic complexes of iscom or iscom matrix and antigens together with an enzyme and possibly also peptides, which specifically binds to a receptor expressed on a cell capable of antigen presentation, and to compositions comprising the new complexes.

BACKGROUND OF THE INVENTION

Exploitation of the mucosal immune system offers several advantages from a vaccine point of view. Mucosal vaccines may achieve both systemic and local mucosal immune protection against infectious micro-organisms of which many gain access to the body via mucosal membranes. There is a growing interest for oral vaccines and for the possibility of using such vaccines to protect against infectious diseases affecting not only mucosal surfaces but also against diseases like HIV, polio etc.

Mucosally active vaccines containing recombinant protein antigens would have many immunological and economic advantages for inducing protective immunity against a wide variety of mucosal and systemic pathogens.

Recent results show that antigens incorporated into iscoms are highly immunogenic by mucosal routes, inducing strong T cell mediated immune responses that include secretory IgA antibodies, Th1 dependent delayed type hypersensitivity (DTH) and cytokine production, as well as very strong class I MHC restricted $CD8^+$ T cell responses. Serum antibody production is also primed, but this is relatively less efficient (3, 11).

The particulate nature of iscoms allows them to preferentially target and activate accessory cells such as macrophages and dendritic cells (DC)(14-17). Iscoms induce normal responses in IL4KO, but not in IL12KO mice (3, 12 and 18). In addition, iscoms stimulate the production of mediators such as IL1, IL6 and IL12 from macrophages and DC and in vivo depletion of macrophages markedly reduces the adjuvant effects of iscoms (15, 18-22).

There is a group of bacterial toxins that exert strong enzymatic activity on mammalian cells, such as E. coli heat-labile toxin (LT) and choler toxin (CT). They act by ADP-ribosylation of GTP-binding proteins in the cell membrane of the target cells, resulting eventually in the formation of large quantities of intracellular cAMP. The increase in cAMP may then act to immunomodulate many diverse immune reactions such as increasing B lymphocyte differentiation, augmenting co-stimulation of antigen-presenting cells, inhibiting or promoting various T cell functions or modulating apoptotis in lymphoid cells. They are therefore potent adjuvants.

CT is composed of five enzymatically inactive, non-toxic B-subunits (CTB) held together in a pentamere structure surrounding a single A-subunit that contains a linker to the pentamere via the A2 fragment (CTA2) and the toxic enzymatically active A1-fragment (CTA1) of the molecule.

The toxic CTA1 has strong ADP-ribosyl transferase activity. This results in activation of adenylate cyclase and the subsequent intracellular increase in cAMP.

CTB binds to the ganglioside GM1-receptor, present on most mammalian cells including lymphocytes and gut epithelial cells. CTB has been integrated in ISCOMS as a mucosa targeting molecule EP 97905539.9 and also together with antigens that do not easily penetrate mucosas EP 97905541.5, in order to direct orally administrated iscoms to the mucosa.

Although it has been shown that CT is a potent inducer of most T cell dependent responses when given orally (3, 4), it has also been reported that it may be less efficient at stimulating $CD4^+$ Th1 cells than Th2 cells (5-7). Furthermore, it is not widely accepted as being able to prime $CD8^+$ T cells, while the toxicity of intact CT is likely to prevent its use as a practical vaccine vector in man. Recently attempts have been made to overcome this problem by using an artificial adjuvant vector composed of the enzymatically active A1 fragment of CT (CTA1) linked to two Ig binding domains of staphylococcal protein A. The resulting CTA1-DD fusion protein binds B lymphocytes specifically, has no systemic toxicity and has similar adjuvant properties to CT holotoxin when given by parenteral routes (8)+. However, preliminary indications are that it may have only limited effects when given orally.

Whereas B lymphocytes play a central role in the adjuvant effects of CT and in particular, CTA1-DD (8, 13), the particulate nature of iscoms allows them to preferentially target and activate accessory cells such as macrophages and dendritic cells (DC) (14-17). Thus, the mucosal adjuvant effects of CT are dependent on the presence of IL4 dependent B cell follicles in Peyer's patches (PP), but not on IL12 (3, 13). In contrast, iscoms show an opposite pattern of requirements, inducing normal responses in IL4KO, but not in IL12KO mice (3, 17, and 18). In addition whereas CT may inhibit many functions of macrophages, iscoms stimulate the production of mediators such as IL1, IL6 and IL12 from macrophages and DC and in vivo depletion of macrophages markedly reduces the adjuvant effects of iscoms (15, 18-22).

Thus, iscoms and CTA1 and its derivatives use different anatomical routes and immune mechanisms to induce mucosal immune responses.

SUMMARY OF THE INVENTION

It has now turned out that when combining iscoms and an enzyme, especially CTA1 and its derivatives, their adjuvant effects are enhanced, some of their limitations and disadvantages are overcome and that the over all effect unexpectedly may be synergistic. Surprisingly the enzymatic activity of CTA1 is kept intact in the complex. This novel formulation is non-toxic and is highly immuogenic by a variety of mucosal and systemic routes.

The main object of the invention is to provide an immunogenic complex comprising at least one glycoside, at least one lipid and at least one antigen which antigen is integrated into an iscom complex or coupled on to or mixed with an iscom complex or iscom matrix complex, characterized in that it also comprises at least one enzyme.

Another object of the invention is to provide immunogenic iscom complexes, comprising at least one glycoside, at least one lipid and at least one antigen, into which an enzyme preferably A1 subunits of a bacterial enterotoxin have been integrated.

Another object is to provide immunogenic iscom complexes into which both enzymes and peptides or proteins, which specifically binds to a receptor expressed on a cell capable of antigen presentation, have been integrated.

Another object is to provide iscom complexes on to which antigens and enzymes and/or peptides or proteins, which specifically binds to a receptor expressed on a cell capable of antigen presentation, have been coupled.

Another object is to provide iscom complexes mixed with antigens and enzymes and/or peptides or proteins, which specifically binds to a receptor expressed on a cell capable of antigen presentation.

Another object of the invention is to provide immunogenic iscom matrix complexes, comprising at least one glycoside and at least one lipid on to which antigens, enzymes and/or peptides or proteins, which specifically binds to a receptor expressed on a cell capable of antigen presentation have been coupled.

Another object is to provide iscom matrix complexes mixed with antigens and enzymes and/or peptides or proteins, which specifically binds to a receptor expressed on a cell capable of antigen presentation.

Still another object is to provide a complex where the enzyme and a peptide or protein which specifically binds to a receptor is bound together into a fusion protein which is integrated into an iscom complex or coupled on to or mixed with an iscom complex or iscom matrix complex.

Still another object is to provide a complex where the enzyme, the peptide or protein which specifically binds to a receptor and an antigen is bound together into a fusion protein, which is integrated into an iscom complex or coupled on to or mixed with an iscom complex or iscom matrix complex.

Another object is to provide a composition comprising the new complexes according to the invention.

DETAILED DESCRIPTION OF THE INVENTION

The invention relates to a immunogenic complex comprising at least one glycoside, at least one lipid and at least one antigen which antigen is integrated into an iscom complex or coupled on to or mixed with an iscom complex or iscom matrix complex, characterized in that it also comprises an enzyme.

The enzyme is preferably an enzyme that confers enzymatic ADP-ribosylating activity as it has turned out that such an enzyme has unexpected adjuvant activity in combination with iscom and iscom matrix complexes. If the enzyme is toxic it is preferred that the toxic put be deleted from the enzyme. Thus, the enzyme may be an enzyme with ADP-ribosylating activity from which a toxic part has been deleted. Especially the enzyme is a native or mutant bacterial toxin, preferably an enterotoxin and specifically a subunit of a toxin that confers enzymatic ADP-ribosylating activity. The enzyme may be selected from Cholera toxin (CT), *E. Coli* heat labile enterotoxin (LT), Pertussis, Clostridia, Shigella and Peudomonas toxins. Most preferably the enzyme is at least one A1 subunit of a bacterial enterotoxin wherein said enterotoxin is selected from the group consisting of cholera toxin (CT) and *E. Coli* heat labile enterotoxin (LT). Such enzymes and subunits and the production thereof are described in U.S. Pat. No. 5,917,026.

According to a preferred form of the invention, the immunogenic complex further comprises at least one peptide or protein, which specifically binds to a receptor expressed on a cell capable of antigen presentation. Preferably the cell expresses MHC Class I or Class II antigen. The antigen-presenting cell may be belong the group consisting of lymphocytes, macrophages, dendritic cells, Langerhans cells and epithelial cells.

Iscom contains at least one glycoside, at least one lipid and at least one type of antigenic substances, especially proteins and peptides and can be produced as described in EP 0 109 942 B1, EP 0 242 380 B1 and EP 0 180 564 B1.

Iscom matrices contain at least one glycoside and at least one lipids. Matrices have an is immunostimulating effect on administration together with antigenic substances, and can be produced as described in EP 0 436 620 B1.

The enzyme and/or the antigen and/or the peptide or protein which specifically binds to a receptor may be integrated into an iscom complex. It is also possible to couple one or mote of these substances an to an iscom complex already containing antigens or on to an iscom matrix complex.

Further is it possible to mix on or more of these substances with iscom or iscom matrices. In such a case the iscom complex may already contain one or more antigens and/or one or more enzymes and/or one or more peptides or proteins, which specifically bind to a receptor.

Thus, the invention relates to a composition comprising iscoms wherein one or more antigens, one or more enzymes or one or more receptor binding peptides or proteins are integrated into, coupled on to or mixed with the iscom complex.

The invention also relates to a composition comprising matrix and one or more antigens, one or more enzymes and one or more receptor binding peptides or proteins coupled on to or mixed with the matrix complex.

The antigen-presenting cells having receptors to which the peptide can bind, are suitably cells capable of antigen presentation especially cells expressing MHC Class I and Class II and may be lymphocytes, such as B-lymphocytes, T-cells, monocytes, macrophages, dendritic cells, Langerhans cells, and epithelial and endothelial cells.

The peptide is a peptide that binds to receptors of the above cells, preferably to an Ig or Fc receptor expressed by said antigen-presenting cell and most preferably to receptors of B-lymphocytes.

Examples of specific targeting peptides are peptides capable of binding to receptors of:

(i) granulocyte-macrophage colony-stimulating factor (GM-CSF) capable of binding to the GM-CSF receptor .alpha./.beta.heterodimer present on monocytes, neutrophils, eosinophils, fibroblasts and endothelial cells, (ii) CD4 and CD8 expressed on T cells which together with the T cell receptor (TcR) act as co-receptors for MHC class II and MHC class I molecules, respectively. MHC class I are expressed on most nucleated cells, whereas MHC class II molecules are expressed on dendritic cells, B cells, monocytes, macrophages, myeloid and erythroid precursor cells and some epithelial cells, (iii) CD 28 and CTLA-4, two homodimeric proteins expressed mainly on T cells which bind to B7 expressed on B cells, (iiii) CD40 present mainly on the surface of mature B cells which interact with gp39 expressed on T cells, (iiiii) different isotypes of the Ig heavy chain constant regions which interact with a number of high or low affinity Fc receptors present on mast cells, basophils, eosinophils, platelets, dendritic cells, macrophages, NK cells and B cells.

According to a particularly preferred embodiment of the invention, said peptide is constituted by protein A or a fragment thereof in single or multiple copies, such as one or more D subunits thereof.

According to the invention, the enzyme and the peptide which specifically binds to a receptor may be bound together into a fusion protein, which may be integrated into an iscom complex or coupled on to or mixed with an iscom complex or iscom matrix complex.

The fusion proteins comprise a sub-unit of a native or mutant bacterial toxin that confers enzymatic ADP-ribosylating activity, and, lined thereto, a peptide. The peptide is preferably such that the resulting fusion protein is in possession of water solubility and capability of targeting the fusion protein to a specific cell receptor different from receptors binding to the native toxin; thereby mediating intracellular uptake of at least said subunit.

An antigen may also be incorporated in the fusion protein. Thus , the antigen, the receptor binding peptide or protein and the enzyme may be used as a single molecule or as different combinations in fusion proteins for integration into iscoms or coupling on to iscoms and/or matrices or mixing iscoms and/or matrices. One or more antigens, one or more receptor binding peptides or proteins and one or more enzymes may be used as single molecules or in the fusion protein.

The integration of the substances and the coupling thereof on to iscoms or iscom matrices maybe done as described in EP 0 109 942 B1, EP 0 242 380 B1 and 0 180 564 B1.

Although the invention is by no means limited hereto it will be exemplified in the following mainly with reference to the sub-unit A1 of cholera toxin or a mutant thereof.

Preferably the fusion protein comprises the A1 subunit of cholera toxic and is fused to one or more copies of protein A or a fragment thereof, such as the D region of said protein A.

One fusion protein denoted CTA1-DD consisting of CTA1 linked to DD, a dimer of the D-region of protein A, binds to soluble immunoglobulins as well as the Ig-receptor on B cells. The results demonstrate that is molecule lacks enterotoxic activity, but still effectively ADP-ribosylates target protein. When used as a parenteral adjuvant CTA1-DD enhances anti-KLH antibody responses and increases KLH T cell priming.

These results demonstrate the possibility to circumvent the toxic effects of CT simply by removing the CTB pentamer, thus excluding the potential interaction resulting in toxicity between the epithelial cell GM1-receptor and CT. The strategy of targeting of the immunomodulating activity of CTA1 to defined cell populations can be expanded to include essentially any given cell type, enabling specific modulation of cellular responses controlled by cAMP, provided that a suitable targeting molecule is available. CTA1 alone is highly insoluble in physiological aqueous solutions. Thus, the targeting molecule used as fusion partner in this invention also has the important function to enhance solubility of the CTA1 entity.

The CTA1 moiety in CTA1-DD is targeted to B cells primarily, and away from the GM1-receptor on e.g. the gut epithelial cells. Furthermore, using this construct it has been demonstrated that
(i) the enzymatic activity of CTA1 was retained in CTA1-fusion proteins provided that CTA1 was fused at its carboxy terminus;
(ii) CTA1 in the fusion protein exerts its ADP-ribosyltransferase activity in target cells through a pathway for entry that is different from the surface ganglioside GM1-receptor; and that.
(iii) CTA1-DD displays a strong immunopotentiating activity.

Similarly, CTA1 may be fused to other targeting molecules such as e.g. CD4 to access MHC II expressing cells or any other ligand that specifically can bind to a receptor present on the cell surface. Using this approach CTA1 will not interact with the GM1-receptor present on most mammalian cells including gut epithelial cells because the CTB portion is lacking in the construct. There fore, CTA1 is given a narrow spectrum of cellular interactions via specific binding to surface Ig or Fc-receptors thereby targeting CTA1 to primary B cells, and macrophages and other Fc-receptor carrying cells.

Fusion proteins may be produced by general biotechnological methods known in the art. Fusion protein CTA1DD may be produced as described in U.S. Pat. No. 5,917,026. Fusion proteins with CTA1DD any be produced using the vector described in FIG. 7 or as described in references 8, 29.

The pharmaceutical compositions may comprise one or more immunogenic complexes according to the invention, together with one or more excipients that are acceptable in pharmaceutical or veterinary products, whereby complexes and components to be mixed therewith may be placed in separate compartments.

The compositions according to the invention will in practice normally be administered orally but may be given topically, or by rectal administration or by injection.

For oral administration tablets and capsules may contain conventional excipients, such as binders, for example syrup, sorbitol, or polyvinyl pyrrolidone; fillers, for example lactose, microcrystalline cellulose, corn starch, calcium phosphate or sorbitol; lubricants, for example magnesium stearate, stearic acid, polyethylene glycol or silica; desintegrants, for example potato starch or sodium starch glycolate, or surfactants, such as sodium lauryl sulphate.

Oral liquid preparations can be in the form of for example water or oil suspensions, solutions, emulsions, syrups or elixirs, or can be supplied as a dry product for constitution with water or another suitable vehicle before use.

A composition according to the invention can be formulated for parenteral administration by injection or continuous infusion. Compositions for injection can be provided in unit dose form and can take a form such as suspension, solution or emulsion in oil or aqueous carriers and can contain formulating agents, such as suspending, stabilizing and/or dispersing agents. Alternatively, the active constituent can be present in powder form for constitution with a suitable carrier, for example sterile pyrogen-free water, before use.

The compositions according to the invention can contain between 0.1 and 99% by weight of the active constituent, suitably from 30 to 95% for tablets and capsules and 3 to 50% for liquid preparations.

The experimental part shows that iscoms containing a fusion protein comprising CTA1-DD linked to the OVA 323-339 peptide epitope, used as a model antigen, were highly immunogenic when given by the subcutaneous, oral or nasal routes, inducing a wide range of systemic T cell dependent immune responses. No toxicity was observed by any route indicating that rationally designed combined vectors consisting of CTA1-DD and iscoms S may provide the basis of potent and safe mucosal vaccines.

Thus, iscoms containing OVA peptide fused to CTA1-DD were immunogenic when given by a variety of routes, including the oral, nasal and parenteral routes. The responses induced included DTH and serum IgG antibodies in vivo, antigen-specific T cell proliferation and γIFN production in vitro. Despite the fact that it was not possible to detect IL5 production when CTA1-DD-ISCOMS primed lymphocytes were restimulated with OVA in vitro, immunised mice were primed for the production of both IgG2a and IgG1 isotypes, indicating that Th1 and Th2 cells were primed in vivo.

The immune responses induced by iscoms containing the OVA peptide fused to the intact CTA1-DD construct were markedly superior to those found after immunisation with iscoms containing the CTA1-R72K-DD construct which contains a point mutation that abolishes the enzymatic activity of CTA1. This confirms our previous findings that ADP-ribosylating function is essential for the adjuvant property of the CTA1-DD Vector (8) and indicates that a significant proporon of the combined ISCOMS-CTA1DD structure also depends on targeting this activity to the immune system. Nevertheless, iscoms containing the enzymatically inert CTA1-R72K-DD molecule did retain some adjuvant activity when given by mucosal or parenteral routes. This may reflect the well-established adjuvant properties of the iscoms themselves, perhaps enhanced by the ability of the DD fragment to target them in vivo, presumably to B lymphocytes. Thus, in addition to being targeted to DC and/or macrophages like conventional iscoms (14-16, 17), the new, combined vector may have the additional ability to interact with B cells, creating a second potential source of APC for T cell priming. In addition to its potent APC targeting properties, the intact CTA1-DD-IS-COMS adjuvant has the great advantage of being able to activate these cells, creating a costimulatory microenvironment for efficient T cell priming. Iscoms induce DC and/or macrophages to produce proinflammatory cytokines such as IL1, IL6 and IL12 in vivo (15, 18-22), while CTA1-DD is a potent co-activator of B cells (8). For these reasons, at least three important features of CTA1-DD-ISCOMS were considered to contribute to their immunogenicity. First they can physically target antigen and adjuvant to distinct APC populations in vivo and via distinct mechanisms. In the case of iscoms, this probably involves phagocytic uptake by mononuclear cells, whereas CTA1-DD involves receptor-mediated binding and uptake by surface immunoglobulin (8). Secondly, the vector contains two active adjuvants, Quil A and the ADP-ribosylating enzyme CTA1, which can stimulate the relevant cells that have taken up the vector. Lastly, insertion of the antigenic construct into the rigid iscoms particle ensures that the antigen and the adjuvants ate delivered directly to the same APC, focussing their effects for optimal T cell priming.

Extremely low doses of OVA peptide were able to prime systemic immunity by both mucosal and parenteral routes using the CTA1-DD-ISCOMS vector, with as little as 150 ng or 750 ng peptide equivalent being effective by the subcutaneous and oral routes respectively. Secondly, although the antigenic epitope used was delivered as part of a large fusion protein inserted in an iscoms particle, it induced strong immune responses that could be recalled with intact OVA protein. This indicates that CTA1-DD fusion protein and the iscoms vector did not interfere with the antigen processing mechanisms, which normally generate this class II MHC-restricted epitope.

Taken together the results suggest that the combined vector gains access to physiologically relevant antigen processing pathways in an extremely efficient manner. Lastly, it is important to emphasise that no toxicity was observed in mice given the combined adjuvant vectors by any route. This contracts with the toxicity occasionally seen using vectors containing intact Quil A (12, 27, 28), but extends our previous findings that the Quadri A fraction of Quil A and the CTA1-DD fusion protein are themselves lacking significant toxicity, despite their potent adjuvant activities. Thus the combined vector should provide a safe means of inducing mucosal and systemic immunity.

Figure 3:
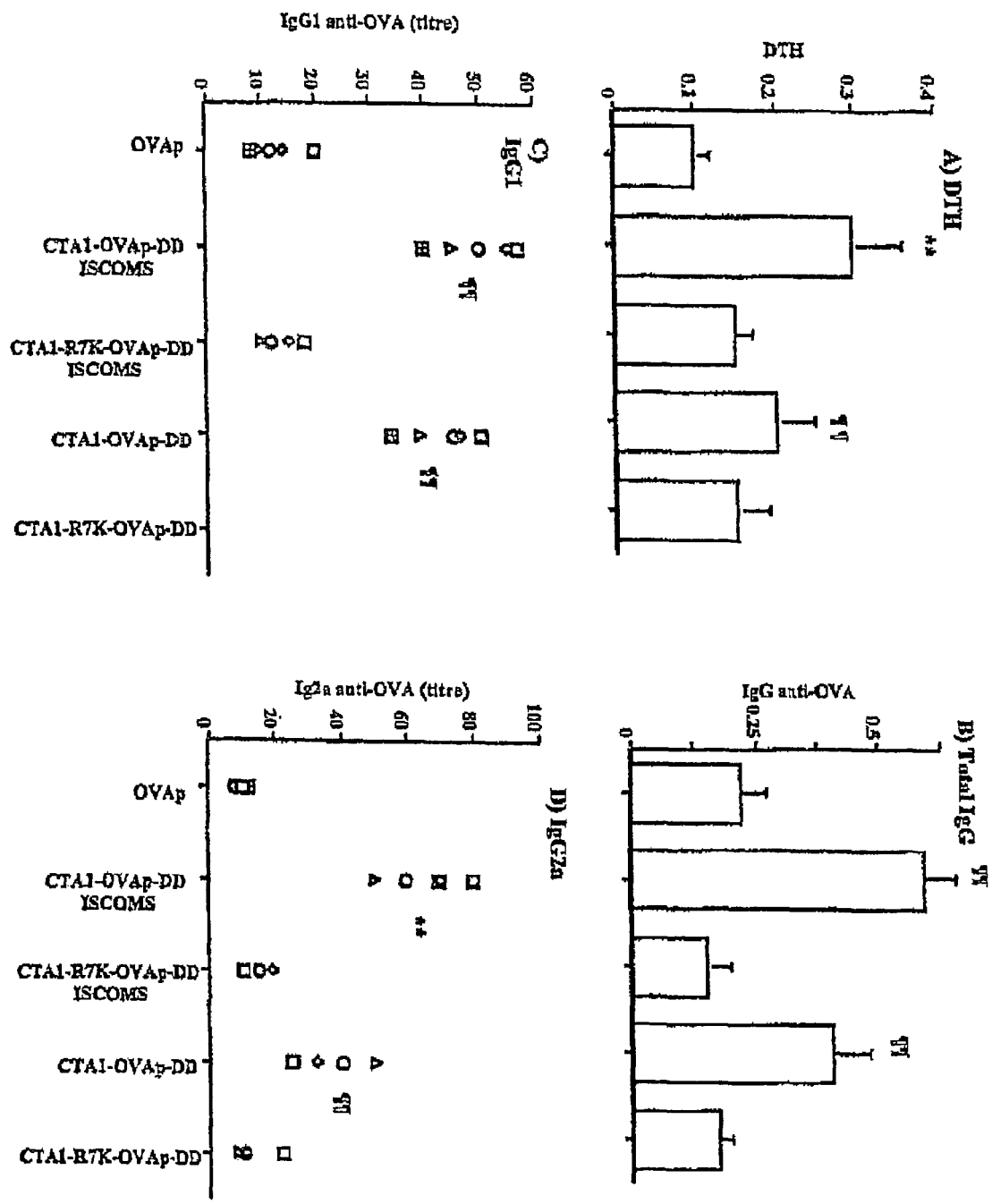

One surprising finding from the study was at the free CTA1-DD fusion protein also had some adjuvant activity when given by the oral route (FIG. 3). As confirmed here, previous studies had shown that this material was active by parenteral and subcutaneous routes (8), but it was considered it unlikely that it would be able to gain access to the B cells necessary for its adjuvant effects when given into the harsh environment of the intestine. However, it is now shown that oral immunization with CTA1-DD containing a defined peptide epitope induces a wide range of immune responses, which interestingly included marked levels of γIFN, despite other claims that CT based adjuvants stimulate predominantly Th2 dependent responses by this route. The responses induced by free CTA1-OVAp-DD were not as high as those, which occurred, when the fusion protein was inserted in iscoms, underlining the added potency of the combined vector. However, the enzymatically inactive CTA-R72K-OVAp protein was unable to induce any response above that generated by peptide alone by the oral or parenteral routes, indicating that the adjuvant properties of the intact CTA1-DD material were dependent on its ADP ribosylating activity, even when give by the oral route.

Figure 4:
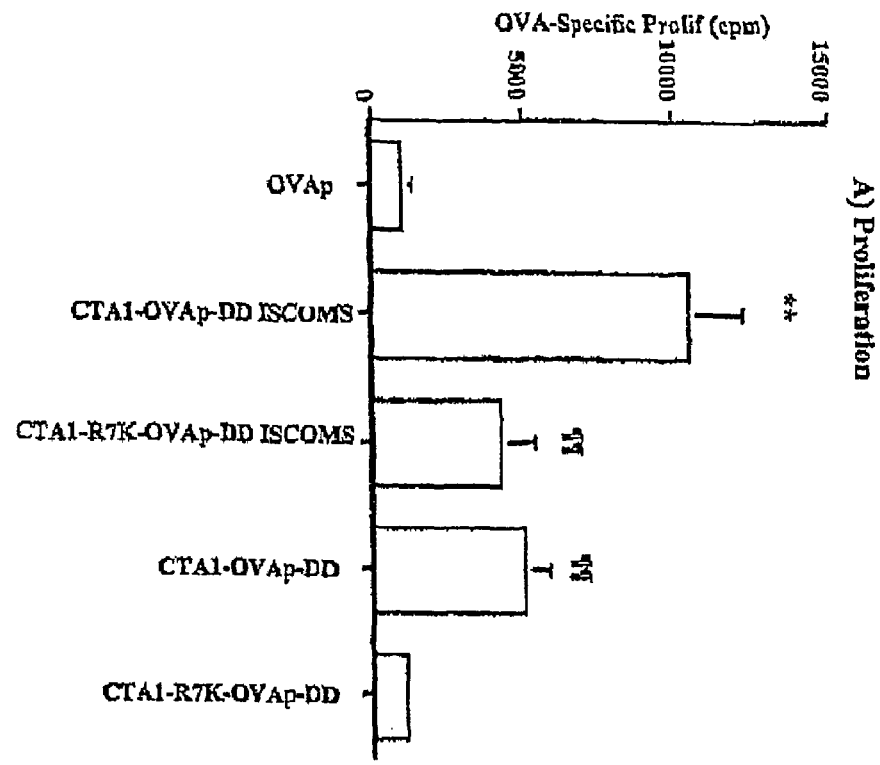
Figure 4:
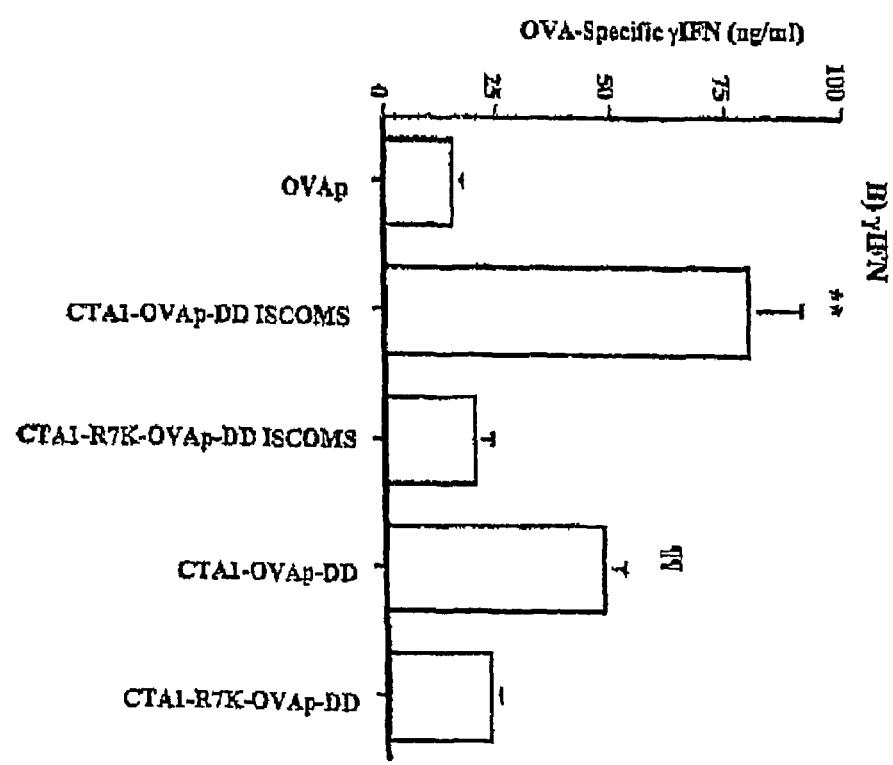

Subcutaneous immunisation gives a synergistic between the CTA1-DD and iscom adjuvant effect in proliferation for CTA1-OVAp-DD-ISCOMS over the sum of the proliferation levels of CTA1-OVAp-DD and CTA1-OVAp-R72K-DD (FIG. 2A). Similarly oral immunisation gives a synergistic effect in IgG2a induction for (FIG. 3D) and in proliferation and γIFN induction for (FIGS. 4A and 4B). Also, intranasal administration gives a synergistic effect in proliferation and γIFN induction as can be seen from FIG. 5.

Together, the results are encouraging evidence that by combining the distinctive adjuvant properties of iscoms and the novel, non-toxic CTA1-DD derivative, it may prove possible to construct effective, safe and stable subunit vaccines which are active by mucosal routes.

All cited references herein are incorporated by reference. The invention will now be further described by non-limiting specific examples with reference to the appended drawings, wherein:

FIGURE LEGENDS

FIG. 1:

Induction of systemic immune responses by subcutaneous immunization with iscoms containing CTA1-OVAp-DD or enzymatically inactive CTA1-R72K-OVAp-DD. Control mice received CTA1-OVAp-DD alone, or OVA 323-339 peptide alone. All mice received the equivalent of 150 ng OVA peptide and results shown are primary DTH responses measured 7 days after immunization (A), serum total IgG (B), IgG1 (C) and IgG2a (D) antibody levels measured 7 days a subcutaneous challenge with soluble OVA given 7 days after primary immunization. The data are means ±1 standard deviation for 5 mice/group and are representative of 3 similar experiments (**, $p<0.05$ vs all other groups; ¶¶, $p<0.05$ vs OVAp alone).

FIG. 2:

Induction of systemic immune responses by subcutaneous immunization with iscoms containing CTA1-OVAp-DD or enzymatically inactive CTA1-R72K-OVAp-DD. Control mice received CTA1-OVAp-DD alone, or OVA 323-339 peptide alone. All mice received the equivalent of 150 ng OVA peptide and results shown are proliferation (A) and γIFN (B) levels measured in draining lymph nodes, measured 7 days after immunization. The data are means ±1 standard deviation for 5 mice/group and are representative of 3 similar experiments (**, $p<0.05$ vs all other groups; ¶¶, $p<0.05$ vs OVAp alone).

FIG. 3:

Induction of systemic immune responses by oral immunization with iscoms containing CTA1-OVAp-DD or enzymatically inactive CTA1-R72K-OVAp-DD. Control mice received CTA1-OVAp-DD alone, CTA1-R72K-OVAp-DD, or OVA 323-339 peptide alone. All mice received the equivalent of 750 ng OVA peptide on 6 occasions and the results shown are primary DTH responses measured 7 days after the last immunization (A), serum total IgG (B), IgG1 (C) and IgG2a (D) antibody levels measured 7 days after a subcutaneous challenge with soluble OVA given 7 days after the last immunization. The data are means ±1 standard deviation for 4-5 mice/group and are representative of 3 similar experiments (**, $p<0.05$ vs all other groups; ¶¶, $p<0.05$ vs OVAp alone).

FIG. 4;

Induction of systemic immune responses by oral immunization with iscoms containing CTA1-OVAp-DD or enzymatically inactive CTA1-R72K-OVAp-DD. Control mice received CTA1-OVAp-DD alone, CTA1-R72K-OVAp-DD, or OVA 323-339 peptide alone. All mice received the equivalent of 750 ng OVA peptide on 6 occasions and the results shown are proliferation (A) and γ IFN (B) levels measured in draining lymph nodes, measured 7 days after immunization. The data are means ±1 standard deviation for 4-5 mice/group and are representative of 3 similar experiments (**, $p<0.05$ vs all other groups; ¶¶, $p<0.05$ vs OVAp alone).

FIG. 5:

Priming of systemic T cells by intranasal immunization with iscoms containing CTA1-OVAp-DD or enzymatically inactive CTA1-R7K-OVAp-DD. Control mice received CTA1-OVAp-DD alone or $OVA_{323-339}$ alone. All mice received the equivalent of 150 ng of OVA peptide, and results shown are proliferation (A) and γ IFN (B) levels measured in the spleen 7 days after immunization. The data are means ±1 SD for five mice per group and are representative of tee similar experiments (**, $p<0.05$ vs all other groups; ¶¶, $p<0.05$ vs OVAp alone).

FIG. 6:

Construction of iscoms consisting of (A) CTA1-OVAp-DD and PR8, (B) CTA1R7K-OVAp-DD and PR8 and (C) PR8 antigens alone. The CTA1-OVAp-DD and CTA1R7K-OVAp-DD were detected by a HRP (horse radish peroxidase) conjugated rabbit antibody binding to the DD domain and the PR8 antigens were detected using biotinylated chicken anti-PR8 immunoglobulin (not binding to the DD domain) followed by HRP conjugated streptavidin. The saponins composing the iscom particle were detected by their absorbance at 210 nm.

FIG. 7:

Linear map of CTA1-OVA-DD sequence (SEQ ID NOS 3-6, respectively, in order of appearance) check:1329 from: 1 to: 3798 CTA1-DD expressions vector with 217 enzymes:*. Max Cuts:1.

FIG. 8:

DNA and amino acid sequence (SEQ ID NOS 1 and 2) of CTA1-DD fusion protein.

EXAMPLE 1

Preparation pf CTA1DD Fusion Protein

Preparation of a Cholera Toxin A1 Subunit (CTA1) Fusion Protein was made as described in U.S. Pat. No. 5,917,026.

*Escherichia coli* strains HB101 and *E. coli* RV308 were used as bacterial hosts for all cloning and expression work. Standard plasmids and vectors used were: pUC 19 and the PCR.TM. vector (Invitrogen, USA). Restriction enzymes and T4 DNA ligase (Boehringer Mannheim, Germany and New England Biolabs, USA) were used according to the recommendation of the supplier.

The oligonucleotides used in the polymerase chain reaction (PCR) were synthesised with an automated machine (Pharmacia-LKB Gene Assembler Plus, Pharmacia Uppsala, Sweden) and phosphorylated separately using polynucleotide kinase (New England Biolabs, USA). Low melting temperature agarose (NUSIEVE.RTM. GTG, FMC Bioproducts, USA) was used to isolate DNA fragments, and Multi Purpose agarose (Boehringer Mannheim, Germany) for DNA analysis.

The PCR amplifications were performed using the DNA Thermal cycler and Taq DNA polymerase (Perkin-Elmer Cetus Instruments, USA).

The bacterial strains were grown in Luria Bertani medium (LB) or yeast tryptone medium (2.times.YT) with ampicillin (Ap) 50 .mu.g/ml or kanaycin (Km) 100 .mu.g/ml. Plasmid DNA was prepared according to MAGIC.RTM. Minipreps DNA Purification Systems manual (Promega, USA).

To determine the nucleotide sequence of the obtained fragments, DNA sequencing was performed using the Sanger method (Sanger, F., Nicklen, S. and Coulson, A. R. DNA sequencing with chain terminating inhibitors. Proc Natl Acad Sci USA. 74, 5463-7, 1977,22). Both strands were sequenced according to a standard protocol for the Taq DYEDEOX-Y.RTM. Terminator cycle sequencing kit (Applied Biosystems, USA). Analyses were performed on an Applied Biosystems Model 373A DNA Sequencing system.

The gene encoding cholera toxin A1 subunit amino acids 1 to 186 (Mekalanos, J. J., Swartz, D. J., Pearson, G. D., Harford, N., Groyne, F. and de, W. M. Cholera toxin genes: nucleotide sequence, deletion analysis and vaccine development. Nature. 306, 551-7, 1983) was obtained by PCR using two synthetic DNA primer (1 and 2 in FIG. 1 of U.S. Pat. No. 5,917,026). Similarly the DNA segment encoding the IgG-binding region D of *staphylococcus aureus* protein A (Uhlen, M., Guss, B., Nilsson B., Gatenbeck, S., Philipson, L. and Lindberg, M. Complete Sequence of the Staphylococcal Gene Encoding Protein A. J. Biol. Chem. 1984) was obtained by PCR using two synthetic DNA primers (3 and 4 in FIG. 1 of U.S. Pat. No. 5,917,026).

Using standard molecular biology techniques as described in Sambrook, J. and al., e. Molecular Cloning—A Laboratory Manual.; Second edition ed.; Cold Spring Harbor Laboratory, Cold Spring Harbor, N.Y.: 19891, plasmid pKP 1001 (FIG. 2 of U.S. Pat. No. 5,917,026) was constructed. Plasmid pKP 1001 contains the gene encoding CTA1 (aa 1-186) fused in frame with a DNA element encoding two tandem copies of the D region from *S. aureus* protein A. In pKP 1001 the transcription unit encoding the CTA1-DD fusion protein is under control of the tryptophane promoter pTrp.

For the production of the CTA1-DD fusion protein, *E. coli* RV308 and HB101 cells transformed with plasmid pKP1001 were grown in shaker flasks overnight in 2 times. YT or LB (250 ml or 500 ml), with kanamycin, at 37.degree. C. After culture, the cells were collected by centrifugation. In order to solubilize the intracellularly produced fusion proteins, which precipitated as inclusion bodies, the cell pellet was treated with 6M Guanidine-HCl. After addition of destined water to 1M Guanidine-HCl to allow the protein to refold, the fusion protein was purified by IgG affinity chromatography using IgG Sepharose (Pharmacia, Sweden). After passage of the solubilized fusion protein through the affinity column the gel was washed with TST (50 mM Tris-HCl, pH 7.4, 150 mM NaCl, 0.05% Tween 20), followed buffered with 10 mM ammonium acetate, pH 4.8. Finally the fusion protein was eluated in 0.2 M acetic acid pH 3.1. The eluted fusion protein was stored in aliquots at −20.degree. C. prior to further use. Two other fusion proteins, one comprising CTA1 fused to DD at its amino terminus (DD-CTA1) and a second (CTA1 (Asp109->Ala)-DD) consisting of a mutant form of CTA1 in which Asp 109 was converted to Ala by PCR-directed in vitro mutagenesis, were prepared in the same way.

EXAMPLE 2

Preparation of Iscoms

Antigens and Adjuvants

Ovalbumin (Fraction V) was obtained from Sigma (Poole, UK), while OVA 323-339 peptide was obtained from Sigma Genosys, CTA1-DD and CTA1-R72K-DD fusion proteins containing the OVA 323-339 epitope were prepared as described in references 8 and 29, CTA1-R72K is a variant of CTA1 from which one amino acid has been deleted and which lacks enzymatic activity.

For the generation of the fusion proteins CTA1-OVAp-DD and CTA1-R7K-OVAp-DD, harbouring one copy of OVA 323-339 between the DD and the CTA1 moieties, a synthetic oligonucleotide encoding OVA 323-339 flanked by nonpalindromic AvaI sites (31) was inserted bead-to-tail into the BbsI site in vectors pCTA1-DD and pCTA1-R7K-DD. For the production of fusion proteins, *Escherichia coli* TG-1 cells transformed with the different expression vectors were grown in 250 ml flasks overnight in 2×YT or Luria-Bertani, with 50 µg/ml kanamycin, at 37° C. After culture, the cells were collected by centrifugation, and the fusion proteins, produced as inclusion bodies, were solubilized by treatment with 6 M guanidine-HCl. After addition of distilled water to allow refolding, the fusion proteins were purified by affinity chromatography on IgG-Sepharose (Pharmacia, Peapack, N.J.) and stored in 0.2 M HAc at 4° C.

Iscom-CTA1-R7K-OVA-DD and Iscom-CTA1-OVA-DD

The preparation of these iscoms was done simultaneously. From the stock solution of protein (1 mg/ml) in 0.2 M acetic acid pH 4, both recombinant proteins (CTA1-OVA-DD and CTA1-R7K-OVA-DD) were each dialysed in refrigerator (4-10° C.) against 0.2 M cold phosphate buffer pH 6.

A one ml sample of each dialysed recombinant solution (equivalent to one mg of each protein) were transferred to room temperature.

One mg purified freeze-dried saponin fraction (Quadri A), normally kept in sealed glass containers in freezer below −18° C., were also transferred to room temperature, opened and the glass container with freeze-dried saponin and a small magnetic bar were arranged with clamps over a magnetic stirrer.

A stock solution of 1% lipid mix (1% cholesterol and 1% phoshatidylcholine dissolved in 20% Mega 10), normally kept in sealed plastic vials in freezer (below −18° C.), were also transferred to room temperature and melted at hand temperature (30-40° C.).

The one mL protein sample were added to the freeze-dried saponin and as soon (a few seconds) the saponin were dissolved in the sired protein solution ten 40 microliter of hand warm 1% lipid mix were added and the mixture stirred for the next 3 hours at room temperature. The mixture were then dialysed for the next 2-3 hours at room temperature against 0,2 M room temperate phosphate buffer pH 6. The dialyse was continued in refrigerator (4-10° C.) for one night. Next day the dialysed protein was centrifuged for 5 minutes at 10000×g and the supernatant (0,9 ml) transferred as a 300 microliter overlay to each of three 4 ml ultra centrifugation plastic vials with preformed sucrose freeze gradient. The freeze gradient was on basis of 25% (W/W) sucrose dissolved in 0,2 M phosphate buffer pH 6.

After 5 hours ultra centrifugation (20° C., sw60 rotor, 50000 rpm, $r_{sv}$=2570000×g) fractions were collected by puncturing the plastic vial with a needle in the bottom. The fractions were analysed for antigenicity, protein content and density. The protein rich fractions, with no free protein were pooled and dialysed in refrigerator (4-10° C.) for 2 days against 0.2 M phosphate buffer pH 6. Finally the iscom preparation was concentrated using centrifugal filter device until desired protein concentration of 0.5 mg/mL was obtained.

Iscom-CTA1DD

This preparation was done as described above using CTA1DD as protein source instead of CTA1-OVA-DD or CTA1-R7K-OVA-DD.

Iscom-Matrix

Saponin Fractionation

Quadri A was prepared as described in Kamstrup S., San Martin R., Doberti A., Grande H., Dalsgaard K,: Preparation and characterisation of quillaja saponin with less heterogeneity than Quil-A. *Vaccine* Vol. 18, No. 21, 1 Apr. 2000.

From aliquots of 10 mg Quadri A saponin/ml $H_2O$ (kept at −20 C) a sample of 2.5 mg saponin (250 microliter) was added to room temperated 2.183 microliter 0.2 M phosphate buffer pH 6, and placed over magnetic stirrer with small magnet in the same way as described above. Fresh thawn 67 microliter room temperated 1.5% lipidmix (1.5% cholesterol and 1.5% phoshatidylcholine dissolved in 20% Mega 10) were then added.

After 3-5 hours stirring at room temperature the resulting 2.5 ml product was dialysed at room temperature one night and day against 0.2 M phosphate buffer pH 6.

Iscoms containing OVA 323-339 peptide were prepared by EP 97905539.9 and EP 97905541.5. Iscom matrix without protein were prepared by mixing 2.5 mg Quadri A in 250 µl $H_2O$ with 2.183 ml 0.2M PBS pH 6 plus 67 µl lipid mix containing 1.5% cholesterol and 1.5% phoshatidylcholine in 20% Mega10 and sting for 3-5 hours at room temperature. The resulting iscoms were dialysed at room temperature for 36 hours against 0.2 M PBS analysed by EM as above.

EXAMPLE 3

Subcutan Immunisation

Animals

BALB/c mice (H-2d) were purchased from Harlan Olac (Bicester, UK) and maintained under SPF conditions in the Central Research Facility, University of Glasgow, or were obtained from B&K (Sollentuna, Sweden) and bred in the Department of Microbiology and Immunology, University of Gothenburg. All animals were first used at 6-8 weeks of age.

Immunisation of Animals

Mice were immunised subcutaneously into one footpad with iscoms or purified fusion proteins containing 4 µg of CTA1-OVAp-DD, equivalent to 150 ng OVA 323-339 in a total volume of 50 µl. One group of mice received 150 ng OVA 323-339 alone.

Measurement of OVA-Specific Immune Responses In Vivo 7 days after the last immunisation, delayed type hypersensitivity (DTH) were assessed by determining the increment in footpad thickness found 24 hours after subcutaneous injection of 100 µg of heat aggregated OVA in 50 µl of sterile saline. Mice were bled for primary serum antibody responses at this time and also 7 days after DTH challenge to assess secondary responses. Secretory IgA antibody responses were measured 7-10 days after the last feed of antigen in intestinal washes obtained after four gavages with PEG as described previously (9). Total IgG, IgA and IgG1 and IgG2a isotype responses were measured by ELISA, as described previously (10). Local antibody responses were measured in the lung.

Measurement of OVA-Specific Immune Responses In Vitro 7 days after the last immunisation, draining popliteal lymph nodes, spleens or cervical lymph nodes were removed and single cell suspensions prepared in RPMI 1640 (Gibco BRL, Paisley, Scotland) by rubbing through a stainless steel mesh and passing the resulting suspension through Nitex mesh (Cadisch & Sons, London, U.K.). After three washes in medium, the cells were resuspended at a final concentration of $10^6$ cells/ml and cultured in 200 μl aliquots in flat bottomed 96 well tissue culture plates (Costar, Nucleopore, High Wycombe, U.K.) in RPMI 1640 containing 10% FCS, 100 U/ml penicillin, 100 mg/ml streptomycin, 50 mg/ml fungizone, 2 mM L-glutamine, 25 mM Hepes, 50 mM 2-mercaptoethanol (all Gibco BRL), either alone or with 1 mg/ml OVA. Proliferation was assessed by addition of 1 μCi/well $^3$H thymidine for the last 18 hours of culture. Cell bound DNA was harvested on filter mats and $^3$H-TdR incorporation measured on a Betaplate counter. To measure cytokine production, $4 \times 10^6$ lymph node cells in 1 ml aliquots were cultured in 24 well tissue culture plates (Costar) either in medium alone or with 1 mg/ml OVA. Supernatants were harvested after 2-4 days and stored at −20° C. until assayed. Cytokine production was quantified using sandwich ELISA techniques described in detail elsewhere (3, 21), using appropriate pairs of capture and biotinylated detecting antibodies (all Pharmingen). Antibody binding was detected using extravidin-peroxidase (Sigma) and TMB substrate as described above. Cytokine concentrations in test supernatants were determined with reference to a standard curve constructed using serial dilutions of recombinant cytokines (Pharmingen).

Statistical Analysis

Results are expressed as means +/− 1 SD and comparisons were made using unpaired two tailed Student's t-test.

Results

Incorporation into Iscoms Enhances the Systemic Immunogenicity of CTA1-DD Adjuvant Vector A. In Vivo Responses Having successfully incorporated the CTA1-OVAp-DD fusion proteins into iscoms, the immunogenicity of the combined vector was compared with the intact fusion protein. Mice were immunised subcutaneously on one occasion and the subsequent systemic immune responses assessed by measuring primary OVA-specific DTH responses, primary and secondary serum antibody responses and in vitro T cell responses in the draining lymph node.

As anticipated, mice immunised with 150 ng OVA 323-339 in saline showed little or no DTH response above background, whereas mice immunised with purified CTA1-OVAp-DD fusion protein containing the same amount of OVA 323-339 had good DTH responses (FIG. 1A). However, animals receiving CTA1-OVAp-DD fusion protein incorporated it ISCOMS had significantly enhanced DTH responses compared with CTA1-OVAp-DD immunised mice (FIG. 1A). Confirming our previous findings that the enzymatically inactive CTA1-R72K fusion protein lacks inherent adjuvant activity (8), mice receiving CTA1-R72K-OVAp alone had no significant DTH responses above background. However, iscoms containing this material were immunogenic, inducing significant primary DTH responses that were markedly less than those found in mice immunised with CTA1-OVAp-DD-ISCOMS (FIG. 1A), presumably reflecting the known adjuvant properties of the iscom vector itself.

Primary serum antibodies reactive with native OVA could not be detected after immunisation with OVAp in any form (data not shown). However, secondary total IgG antibody responses did occur after subcutaneous challenge with heat aggregated OVA in animals primed with immunogenic vectors. These followed a similar pattern to the DTH responses, with the highest levels of IgG anti-OVA being found in mice immunised with CTA1-OVAp-DD-ISCOMS (FIG. 1B). Significant but lower, IgG responses also occurred in mice given intact CTA1-OVAp-DD fusion protein and in animals receiving CTA1-OVAp-R72K-DD-ISCOMS, whereas mice immunised with OVAp alone or enzymatically inactive CTA1-OVAp-R72K-DD had little or no total IgG antibody in serum (FIG. 1B).

Interestingly, immunisation with CTA1-OVAp-DD-ISCOMS or with CTA1-OVAp-DD primed for both IG1 and IgG2a antibody responses (FIGS. 1C/D), suggesting no bias towards priming of Th1 or Th2 cells by the vectors. Again, some IgG1 and IgG2a responses were found in mice given CTA1-OVAp-R72K-DD-ISCOMS, but not in mice immunised with CTA1-OVAp-R72K-DD itself or with OVAp alone.

B. T Cell Responses In Vitro

Next the immunogenicity of the combined adjuvant vectors was explored in more detail by examining their ability to primed T cell proliferation and cytokine production. Draining popliteal lymph nodes were removed 7 days after primary immunisation and lymphocytes restimulated in vitro with native OVA.

Figure 2:
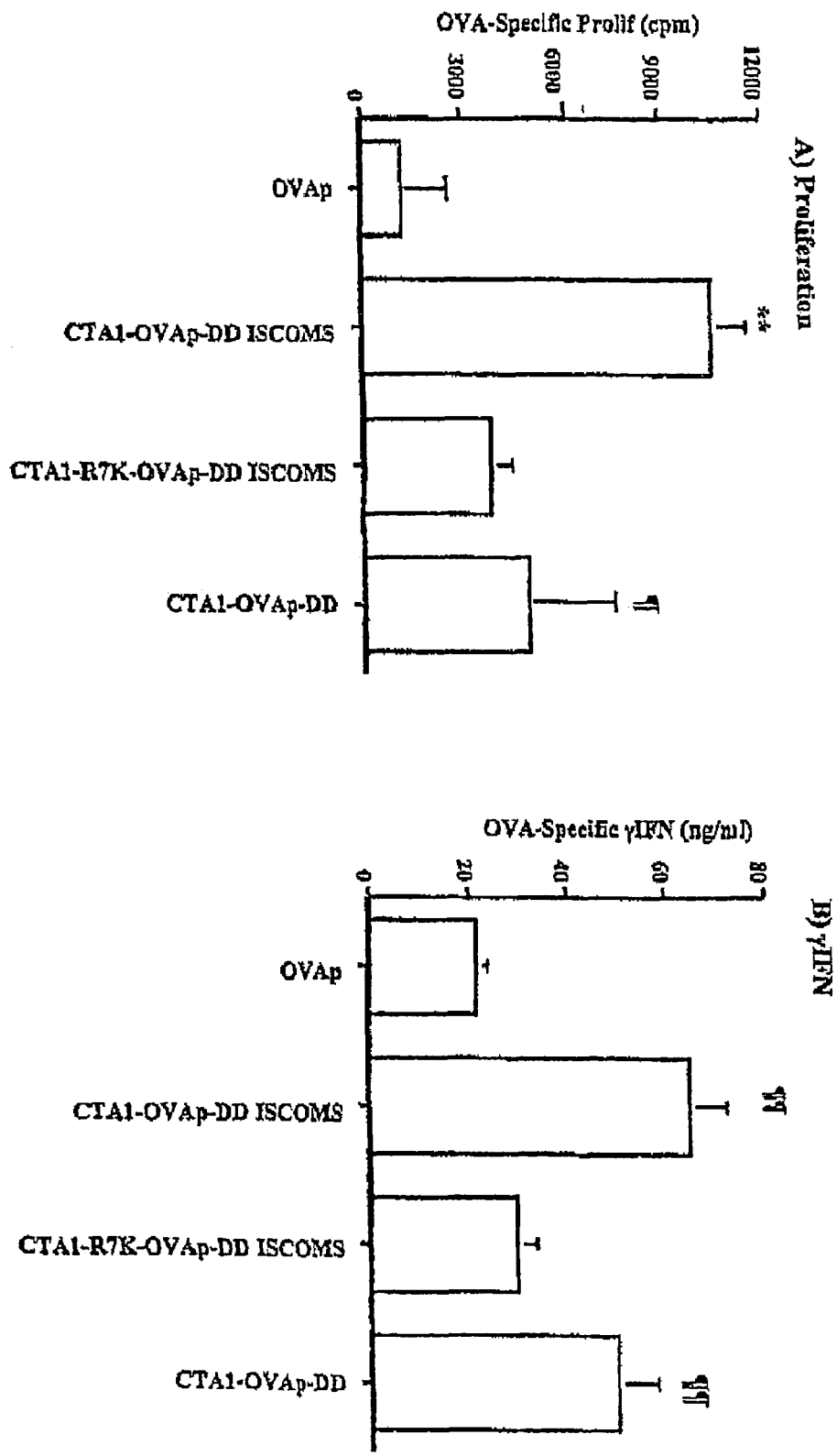

As before, mice immunised with CTA1-OVAp-DD-ISCOMS were primed for very strong T cell proliferation (FIG. 2A) and production of γ IFN (FIG. 2B). Little or no IL5 production was observed. Immunisation with CTA1-OVAp-DD alone, or with iscoms containing the enzymatically inactive CTA1-R72K fusion protein also induced good T cell responses in vitro, although these were significantly lower than those found in CTA1-OVAp-DD-ISCOMS primed animals. Little or no proliferation or cytokine production was observed in mice receiving OVAp alone (FIG. 2). There is a synergistic effect in proliferation for CTA1-OVAp-DD-ISCOMS over the sum of the proliferation levels of CTA1-OVAp-DD and CTA1-OVAp-R72 K-DD (FIG. 2A)

Together, these results confirm that enzymatically active CTA1-DD is an effective adjuvant for a broad range of systemic immune responses when given by parenteral routes and extend earlier findings by showing that incorporation into iscoms markedly enhances this activity.

EXAMPLE 4

Oral Immunisation

Animals were the same as used in example 3. For oral immunisation, mice were fed on days 1, 2, 3, 8, 9 & 10 with iscoms or purified fusion proteins containing 4 μg of CTA1-OVAp-DD, equivalent to 150 ng OVA 323-339. One group of mice received 750 ng OVA 323-339 on each occasion. In vivo and in vivo measurements were performed as in example 3

Results

Incorporation into Iscoms Enhances the Mucosal Immunogenicity of CTA1-DD Adjuvant Vector Earlier work show that CTA1-DD functions poorly as an adjuvant by the oral route. However, iscoms are extremely effective when given orally and therefore it was examined if incorporation into iscoms could improve the mucosal adjuvant properties of CTA1-DD.

A. In Vivo Responses

Mice were fed on six occasions with the different vectors, a protocol found to be optimal in previous work with iscoms, and systemic immune responses assessed as described above. Oral immunisation with CTA1-OVAp-DD-ISCOMS induced significant DTH responses compared with background levels and these were equivalent to those obtained after subcutaneous priming (FIG. 3A). In these experiments, CTA1-DD itself also primed systemic DTH by the oral route, although to a significantly lesser degree than when incorporated into iscoms. As with the parenteral route, enzymatically inactive CTA1-R72K fusion protein lacks inherent adjuvant activity and mice receiving CTA1R72K-OVAp orally induced no significant DTH responses, but this material was immunogenic when incorporated into iscoms, confirming the inherent mucosal adjuvant properties of iscoms. Again this response was markedly less than that found with iscoms containing intact CTA1-DD protein (FIG. 3A). Mice fed 150 ng OVA 323-339 in saline showed little or no DTH response above background, whereas mice immunised with purified CTA1-OVAp-DD fusion protein containing the same amount of OVA 323-339 had good DTH responses. However, animals receiving CTA1-OVAp-DD fusion protein incorporated in iscoms had significantly enhanced DTH responses compared with CTA1-OVAp-DD immunised mice (FIG. 3A).

Primary serum antibodies reactive with native OVA could not be detected after immunisation with OVAp in any form (data not shown). However, secondary total IgG antibody responses did occur after subcutaneous challenge with heat aggregated OVA in animals primed with immunogenic vectors. These followed a similar pattern to the DTH responses, with the highest levels of IgG anti-OVA being found in mice immunised with CTA1-OVAp-DD-ISCOMS (FIG. 3B). Significant, but lower, IgG responses also occurred in mice given intact CTA1-OVAp-DD fusion protein and in animals receiving CTA1-OVAp-R72K-DD-ISCOMS, whereas mice immunised with OVAp alone or enzymatically inactive CTA1-OVAp-R72K-DD had little or no total IgG antibody in serum (FIG. 3B).

Interestingly, immunisation with CTA1-OVAp-DD-ISCOMS or with CTA1-OVAp-DD primed for both IgG1 and IgG2a antibody responses (FIGS. 3C & D), suggesting no bias towards priming of Th1 or Th2 cells by the vectors. Again, some IgG1 and IgG2a responses were found in mice given CTA1-OVAp-R72K-DD-ISCOMS, but not in mice immunised with CTA1-OVAp-R72K-DD itself or with OVAp alone. There is a synergistic effect in IgG2a induction for CTA1-OVAp-DD-ISCOMS over the sum of the IgG2a levels of CTA1-OVAp-DD and CTA1-OVAp-R72K-DD (FIG. 3D)

B. T Cell Responses In Vitro

As before, mice immunised with CTA1-OVAp-DD-ISCOMS were primed for very strong T cell proliferation and production of γIFN (FIGS. 4A & 4B). Immunisation with CTA1-OVAp-DD alone, or with iscoms containing the enzymatically inactive CTA1-R72K fusion protein also induced good T cell responses in vitro, although these were significantly lower than those found in CTA1-OVAp-DD-ISCOMS primed animals. Little or no proliferation or cytokine production was observed in mice receiving OVAp alone. There are synergistic effects in proliferation and γIFN induction for CTA1-OVAp-DD-ISCOMS over the sum of the proliferation and γIFN levels respectively of CTA1-OVAp-DD and CTA1-OVAp-R72K-DD (FIGS. 4A and 4B)

The results show that a targeted CT derivative can be incorporated into iscoms. The resulting combined vector is a potent adjuvant for inducing a wide range of immune responses to small amounts of peptide immunogen after mucosal and parenteral administration.

EXAMPLE 5

Intranasal Immunisation

Mice were immunized intranasally on three occasions 10 days apart, with iscoms or purified fusion proteins containing 4 µg of CTA1-OVAp-DD or CTA1R7K-OVAp-DD (equivalent to 150 ng of $OVA_{323-339}$) in a total volume of 20 µl. Control groups of mice.

Figure 5:
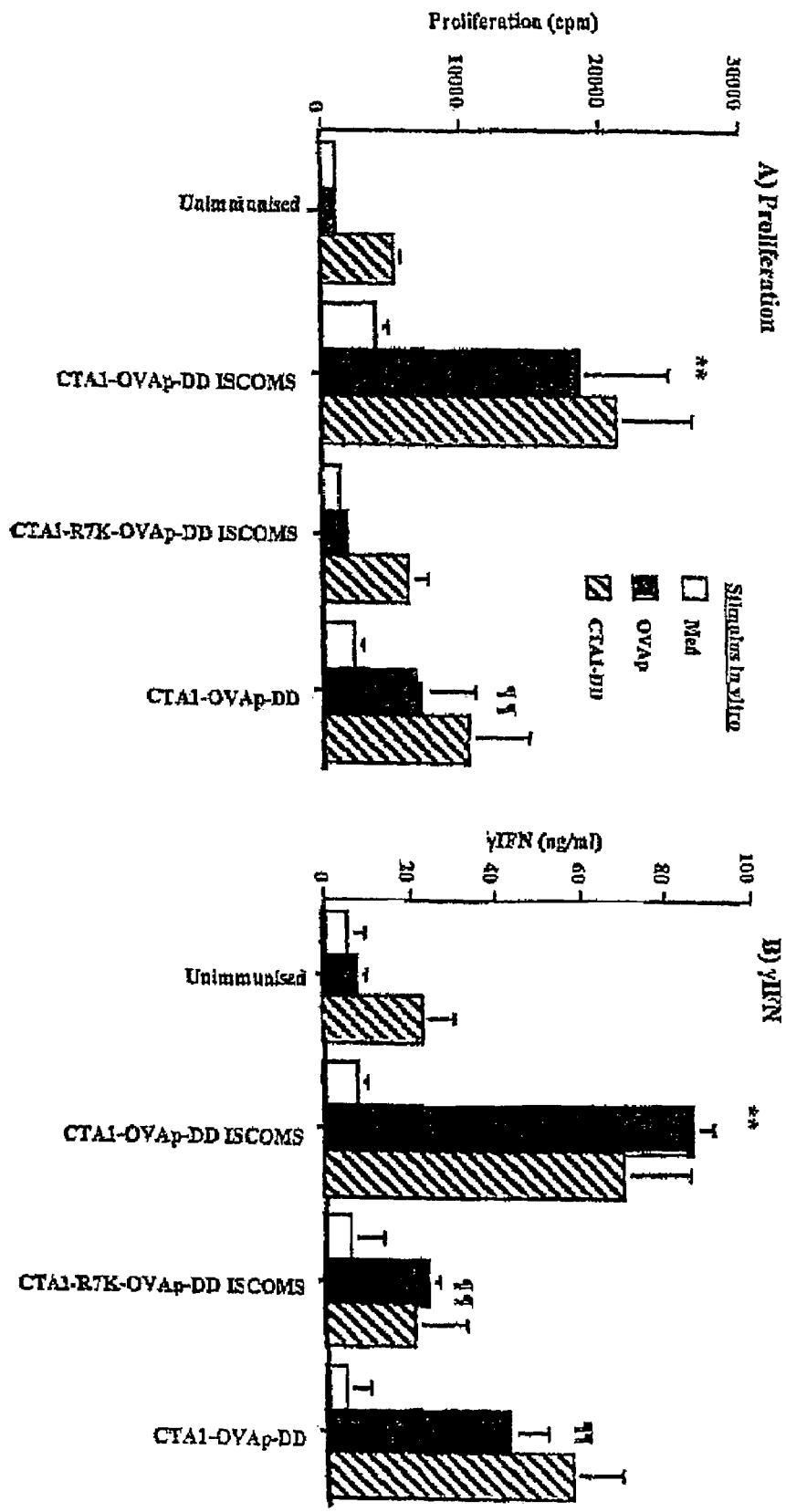

All mice received the equivalent of 150 ng of OVA peptide. FIG. 5 shows the proliferation (A) and IFN-γ (B) levels measured in the spleen 7 days after immunization. It can be seen that there is a synergistic effect in that the level of proliferation and production of IFN-γ when CTA1-OVAp-DD iscoms are used is higher than the sum of the corresponding levels when CTA1R7K-OVAp-DD iscoms are used and CTA1-OVAp-DD.

EXAMPLE 6

Mixed Iscoms Containing Two Antigens

Mixed iscoms containing both CTA1-OVAp-DD and additional antigens (haemagglutinin and neuraminidase from human influenza virus) were prepared essentially according to Example 2.
(A) 0.5 mg of each CTA1R7K-OVAp-DD and detergent solubilized PR8 antigens were mixed with 5 mg of saponin (Spikoside, Isconova, Sweden; 100 mg/ml in distilled water) and 1 mg of each cholesterol and phosphatidyl choline (15 mg/ml in 20% MEGA-10).
(B) 0.5 mg of each CTA1-OVAp-DD and detergent solubilized PR8 antigens were mixed with 5 mg of saponin (Spikoside, Isconova, Sweden; 100 mg/ml in distilled water) and 1 mg of each cholesterol and phosphatidyl choline (15 mg/ml in 20% MEGA-10).
(C) 1.0 mg of detergent solubilized PR8 antigens were mixed with 5 mg of saponin (Spikoside, Isconova, Sweden; 100 mg/ml in distilled water) and 1 mg of each cholesterol and phosphatidyl choline (15 mg/ml in 20% MEGA-10).

Figure 6A:
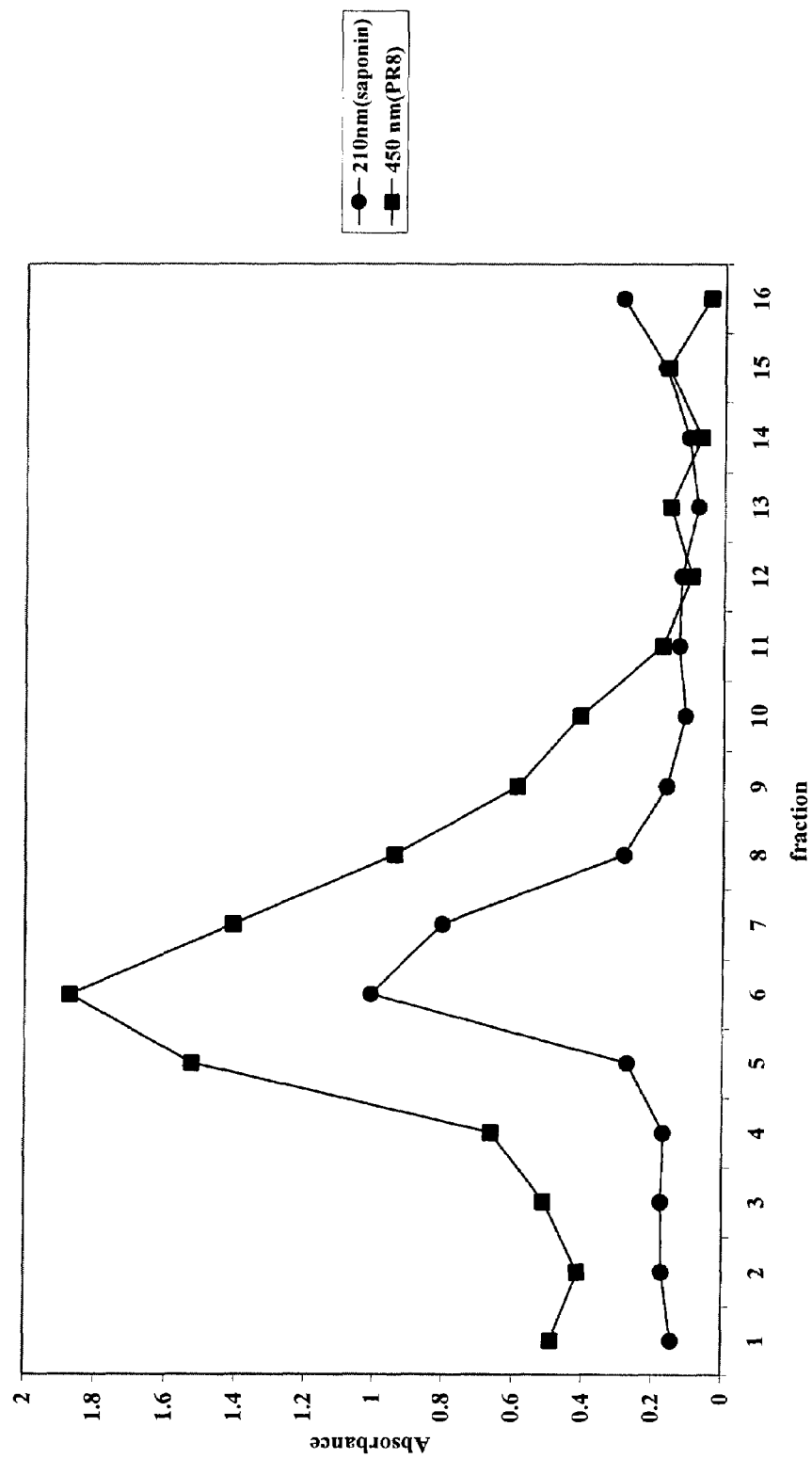
Figure 6C:
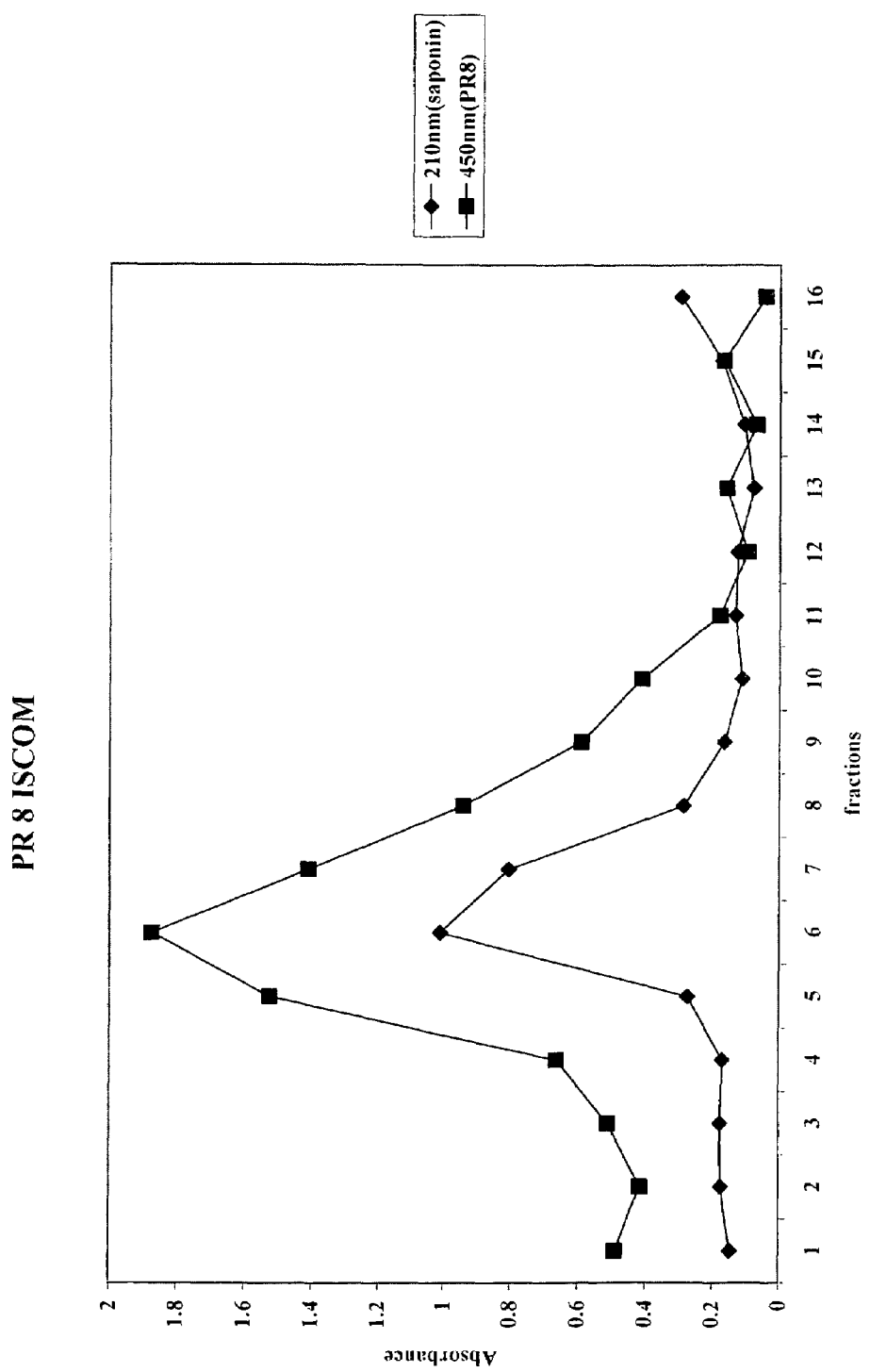

The Iscoms were prepared as known in the art (ref. 34). Aliquots of both preparations were analysed by sucrose density gradient centrifugation. The gradients were divided into fractions that were analysed for saponin content (A210) and the two antigens using ELISA. As shown in FIG. 6 both antigens were simultaneously incorporated into the same complex.

Mice were immunised subcutaneously and orally as described in Example 2. Antibody and systemic T cell responses were recorded against OVA and PR8. As shown for OVA in example 2, the response (antibody IgG1 and IgG2a, proliferation and IFN-γ production were enhanced significantly by the simultaneous incorporation of CTA1-OVAp-DD molecule compared to iscoms containing PR8 antigens alone or combined with CTA1R7K-OVAp-DD.

REFERENCES

1. Mowat, A. M. 1999. Oral tolerance: basic mechanisms and clinical applications. *Curr Opinion Gastroenterol* 15:546.
2. Strobel, S., and A. M. Mowat. 1998. Immune responses to dietary antigens: Oral tolerance. *Immunology Today* 19:173.

3. Grdic, D., R. E. Smith, A. M. Donachie, M. Kjerrulf, E. Hornquist, A. M. Mowat, and N. Lycke. 1999. The mucosal adjuvant effect of cholera toxin and ISCOMS differ in their requirement for IL-12, indicating different pathways of action. *Eur J Immunol* 29:1774.
4. Wilson, A. D., M. Bailey, N. A. Williams and C. R. Stokes. 1991. The in vitro production of cytokines by mucosal lymphocytes immunized by oral administration of keyhole limpet hemocyanin using cholera toxin as an adjuvant. *Eur. J. Immunol* 21:2333.
5. McGhee, J. R., C. Czerkinsky, and J. Mestecky. 1999. Mucosal vaccines: an overview. In *Mucosal immunology, 2nd edition*. P. L. Ogra, 3J Mestecky, M. E. Lamm, W. Strober, J. R. McGhee, and J. Bienenstock, eds. Academic Press, San Diego, p. 741.
6. McGhee, J. R., J. Mestecky, M. T. Dertzbaugh, J. H. Eldridge, M. Hirasawa, and H. Kiyono. 1992. The mucosal immune system: from fundamental concepts to vaccine development, *Vaccine* 10:75.
7. Elson, C. O., and M. T. Dertzbaugh. 1999. Mucosal Adjuvants. In *Mucosal Immunology, 2nd Edition*. P. L. Ogra, J. Mestecky, M. E. Lamm, W. Strober, J. R. McGhee, and J. Bienenstock, eds. Academic Press, San Diego, p. 818.
8. Agren, L. C., L. Ekman, B. Lowenadler, J. G. Nedrud, and N. Lycke. 1999. Adjuvanticity of the cholera toxin A1-based gene fusion protein, CTA1-DD, is critically dependent on the ADP-ribosyltransferase and Ig-binding activity. *J. Immunol* 162:2432.
9. Mowat, A. M., K. J. Maloy, and A. M. Donachie. 1993. Immune stimulating complexes as adjuvants for inducing local and systemic immunity after oral immunisation with protein antigens. *Immunology* 80:527.
10. Maloy, K. J., A. M. Donachie, and A. M. Mowat. 1995. Induction of Th1 and Th2 CD4+ T cell responses by oral or parenteral immunization with ISCOMS. *Eur J Immunol* 25:2835.
11. Smith, R. E., A. M. Donachie, and A. M. Mowat. 1998. Immune stimulating complexes as mucosal adjuvants. *Immunol Cell Biol* 76:263.
12. Sjolander, A., J. C. Cox, and I. G. Barr. 1998. ISCOMs: an adjuvant with multiple functions. *J Leuk Biol* 64:713.
13. Vajdy, M., M. H. Kosco-Vilbois, M. Kopf, G. Kohler, and N. Lycke. 1995. Impaired mucosal immune responses in Interleukin 4-targeted mice. *J. Exp. Med.* 181:41.
14. Claassen, I. J. T. M., A. D. M. E. Osterhaus, and E. Claassen. 1995. Antigen detection in vivo after on with different presentation forms of rabies virus antigen: Involvement of marginal metallophilic metaophages in the uptake of immune-stimulating complexes. *Eur J Immunol* 25:1446.
15. Claassen, I. J. T. M., A. D. M. E. Osterhaus, M. Poelen, N. Van Rooijen, and E. Claassen. 1998. Antigen detection in vivo after immunization with different presentation forms of rabies virus antigen, II. Cellular, but not humoral systemic immune responses against rabies virus immune stimulating complexes are macrophage dependent *Immunology* 94:455.
16. Watson, D. L., N. A. Watson, C. Fossum, K. Lovgren, and B. Morein. 1992. Interactions between immune-stimulating complexes (ISCOMs) and peritoneal mononuclear leucocytes. *Microbiol Immunol* 36:199.
17. Smith, R. E., A. M. Donachie, D. Grdic, N. Lycke, and A. M. Mowat. 1999. Induction of innate immune responses by immune simulating complexes: a critical role for IL12 in the immunogenicity of ISCOMS. *J Immunology* 162:5536.
18. Smith, R. E., A. M. Donachie, F. H. McLaren, and A. M. Mowat. 1998. Preservation of mucosal and systemic adjuvant properties of ISCOMS in the absence of functional interleukin 4 or g interferon. *Immunology* 93:556.
19. Villacres-Eriksson, M., S. Behboudi, A. J. Morgan, G. Trinchieri, and B. Morein. 1997. Immunomodulation by Quillaja saponaria adjuvant formulations: in vivo stimulation of interleukin 12 and its effects on the antibody response. *Cytokine* 9:73.
20. Behboudi, S., B. Morein, and M. Villas-Eriksson. 1997. In vivo and in vitro induction of IL-6 by Quillaja saponaria molina triterpenoid formulations. *Cytokine* 9:682.
21. Behboudi, S., B. Morein, and M. Villacres-Eriksson. 1996. In vitro activation of antigen-presenting cells (APC) by defined composition of Quillaja saponaria Molina triterpenoids. *Clinical & Experimental Immunology* 105:26.
22. Mowat, A. M., R. E. Smith, A. M. Donachie, E. Furrie, D. Grdic, and N. Lycke. 1999. Oral vaccination with Immune stimulating complexes. *Immunology Letters* 65:133.
23. Kamstrup, S., R. San Martin, A. Doberti, H. Grande, and K. Dalsgaard 2000. Preparation and characterisation of Quillaja saponin with less heterogeneity than Quil-A. *Vaccine* 18.
24. Heeg, K., W. Kuon, and H. Wagner. 1991. Vaccination of Class I major histocompatability complex (MHC)-restricted murine CD8+ cytotoxic T lymphocytes toward soluble antigen: immunostimulating complexes enter the Class I MHC-restricted antigen pathway and allow sensitization against the immunodominant peptide. *Eur. J. Immunol*, 21:1523.
25. Takahashi, H., T. Takeshita, B. Morein, S. Putney, R. N. Germain, and J. Berzofsky. 1990. Induction of $CD8^+$ cytotoxic T cells by immunisation with purified HIV-1 envelope protein in ISCOMS. *Nature* 344:873.
26. Mowat, A. M., A. M. Donachie, G. Reid, and O. Jarrett. 1991. Immune stimulating complexes containing Quil A and protein antigen prime Class I MHC-restricted T lymphocytes in vivo and are active by the oral route. *Immunology* 72:317.
27. Morein, B., K. Lovgren, B. Ronnberg, A. Sjolander, and M. Villacres-Erikisson 1995. Immunostimulating complexes. Clinical potential in vaccine development. *Clin. Immunother.* 3:461.
28. Johansson, M., K. Morein and K. Lovgren-Bengtsson. 1999. Iscoms with different Quillaja saponin components differ in their immunomodulating activities. *Cell Immunol: In Press*.
29. Agren, L. C. Ekman, B. Lowenadler and N. Y. Lycke 1997. Genetically engineered nontoxic vaccine adjuvant that combines B cell targeting with immunomodulation by cholera toxin A1 subunit. *J. Immunol.* 158:3936.
30. Lovgren, K., Kaberg, H. and Morein, B. (1990). An experimental influenza subunit vaccine (ISCOM)—induction of protective immunity to challenge infection in mice after intranasal or subcutaneous administration. *Clin. exp. Immunol.* 82, 435-439.
31. Lowenadler, B., A. M. Svennerholm, M. Gidlund, E. Holmgren, K. Krook, C. Svanholm S. Ulf. and S. Josephson. 1990. Enhanced immunogenicity of recombinant peptide fusions comprising multiple copies of a heterologous T helper epitope. *Euro. J. Immunol*, 20:1541.

SEQUENCE LISTING

<160> NUMBER OF SEQ ID NOS: 6

<210> SEQ ID NO 1
<211> LENGTH: 1029
<212> TYPE: DNA
<213> ORGANISM: Artificial Sequence
<220> FEATURE:
<223> OTHER INFORMATION: Description of Artificial Sequence: DNA
      encoding CTA1-DD f -continued

```
Arg Asn Gly Phe Ile Gln Ser Leu Lys Asp Asp Pro Ser Gln Ser Thr
                245                 250                 255 aac gtt tta ggt gaa gct aaa aaa tta aac gaa tct caa gca ccc aaa      816
Asn Val Leu Gly Glu Ala Lys Lys Leu Asn Glu Ser Gln Ala Pro Lys
            260                 265                 270 ccc gag gct gat gcg caa caa aat aac ttc aac aaa gat caa caa agc      864
Pro Glu Ala Asp Ala Gln Gln Asn Asn Phe Asn Lys Asp Gln Gln Ser
        275                 280                 285 gcc ttc tat gaa atc ttg aac atg cct aac tta aac gaa gcg caa cgt      912
Ala Phe Tyr Glu Ile Leu Asn Met Pro Asn Leu Asn Glu Ala Gln Arg
    290                 295                 300 aac ggc ttc att caa agt ctt aaa gac gac cca agc caa agc act aac      960
Asn Gly Phe Ile Gln Ser Leu Lys Asp Asp Pro Ser Gln Ser Thr Asn
305                 310                 315                 320 gtt tta ggt gaa gct aaa aaa tta aac gaa tct caa gca ccc aaa ccc     1008
Val Leu Gly Glu Ala Lys Lys Leu Asn Glu Ser Gln Ala Pro Lys Pro
                325                 330                 335 gag gta gca ggt cag aat tag                                         1029
Glu Val Ala Gly Gln Asn
            340

<210> SEQ ID NO 2
<211> LENGTH: 342
<212> TYPE: PRT
<213> ORGANISM: Artificial Sequence
<220> FEATURE:
<223> OTHER INFORMATION: Description of Artificial Sequence: CTA1-DD
      fusion protein <400> SEQUENCE: 2

Met Lys Ala Ile Phe Val Leu Lys Ala Ser Asn Asp Asp Lys Leu Tyr
  1               5                  10                  15

Arg Ala Asp Ser Arg Pro Pro Asp Glu Ile Lys Gln Ser Gly Gly Leu
             20                  25                  30

Met Pro Arg Gly Gln Ser Glu Tyr Phe Asp Arg Gly Thr Gln Met Asn
         35                  40                  45

Ile Asn Leu Tyr Asp His Ala Arg Gly Thr Gln Thr Gly Phe Val Arg
     50                  55                  60

His Asp Asp Gly Tyr Val Ser Thr Ser Ile Ser Leu Arg Ser Ala His
 65                  70                  75                  80

Leu Val Gly Gln Thr Ile Leu Ser Gly His Ser Thr Tyr Tyr Ile Tyr
                 85                  90                  95

Val Ile Ala Thr Ala Pro Asn Met Phe Asn Val Asn Asp Val Leu Gly
            100                 105                 110

Ala Tyr Ser Pro His Pro Asp Glu Gln Glu Val Ser Ala Leu Gly Gly
        115                 120                 125

Ile Pro Tyr Ser Gln Ile Tyr Gly Trp Tyr Arg Val His Phe Gly Val
    130                 135                 140

Leu Asp Glu Gln Leu His Arg Asn Arg Gly Tyr Arg Asp Arg Tyr Tyr
145                 150                 155                 160

Ser Asn Leu Asp Ile Ala Pro Ala Ala Asp Gly Tyr Gly Leu Ala Gly
                165                 170                 175

Phe Pro Pro Glu His Arg Ala Trp Arg Glu Glu Pro Trp Ile His His
            180                 185                 190

Ala Pro Pro Gly Cys Gly Asn Ala Pro Arg Ser Ser Gly Ser Gly Lys
        195                 200                 205

Thr Pro Glu Ala Asp Ala Gln Gln Asn Asn Phe Asn Lys Asp Gln Gln
    210                 215                 220

```
Ser Ala Phe Tyr Glu Ile Leu Asn Met Pro Asn Leu Asn Glu Ala Gln
225                 230                 235                 240

Arg Asn Gly Phe Ile Gln Ser Leu Lys Asp Asp Pro Ser Gln Ser Thr
            245                 250                 255

Asn Val Leu Gly Glu Ala Lys Lys Leu Asn Glu Ser Gln Ala Pro Lys
            260                 265                 270

Pro Glu Ala Asp Ala Gln Gln Asn Asn Phe Asn Lys Asp Gln Gln Ser
        275                 280                 285

Ala Phe Tyr Glu Ile Leu Asn Met Pro Asn Leu Asn Glu Ala Gln Arg
        290                 295                 300

Asn Gly Phe Ile Gln Ser Leu Lys Asp Asp Pro Ser Gln Ser Thr Asn
305                 310                 315                 320

Val Leu Gly Glu Ala Lys Lys Leu Asn Glu Ser Gln Ala Pro Lys Pro
            325                 330                 335

Glu Val Ala Gly Gln Asn
            340
```

<210> SEQ ID NO 3
<211> LENGTH: 3798
<212> TYPE: DNA
<213> ORGANISM: Artificial Sequence
<220> FEATURE:
<223> OTHER INFORMATION: Description of Artificial Sequence: Synthetic expression vector
<220> FEATURE:
<221> NAME/KEY: CDS
<222> LOCATION: (1)..(3798)

<400> SEQUENCE: 3

```
gtg cct cac tga tta agc att ggt aac tgt cag acc aag ttt act cat      48
Val Pro His     Leu Ser Ile Gly Asn Cys Gln Thr Lys Phe Thr His
1                 5                  10                  15 ata tac ttt aga ttg att taa aac ttc att ttt aat tta aaa gga tct      96
Ile Tyr Phe Arg Leu Ile     Asn Phe Ile Phe Asn Leu Lys Gly Ser
                20                  25                  30 agg tga aga tcc ttt ttg ata atc tca tga cca aaa tcc ctt aac gtg     144
Arg     Arg Ser Phe Leu Ile Ile Ser     Pro Lys Ser Leu Asn Val
                    35                      40 agt ttt cgt tcc act gag cgt cag acc ccg tag aaa aga tca aag gat     192
Ser Phe Arg Ser Thr Glu Arg Gln Thr Pro     Lys Arg Ser Lys Asp
45                  50                          55 ctt ctt gag atc ctt ttt ttc tgc gcg taa tct gct gct tgc aaa caa     240
Leu Leu Glu Ile Leu Phe Phe Cys Ala     Ser Ala Ala Cys Lys Gln
60                  65                      70 aaa aac cac cgc tac cag cgg tgg ttt gtt tgc cgg atc aag agc tac     288
Lys Asn His Arg Tyr Gln Arg Trp Phe Val Cys Arg Ile Lys Ser Tyr
75                  80                  85                  90 caa ctc ttt ttc cga agg taa ctg gct tca gca gag cgc aga tac caa     336
Gln Leu Phe Phe Arg Arg     Leu Ala Ser Ala Glu Arg Arg Tyr Gln
                95                  100                 105 ata ctg tcc ttc tag tgt agc cgt agt tag gcc acc act tca aga act     384
Ile Leu Ser Phe     Cys Ser Arg Ser     Ala Thr Thr Ser Arg Thr
                110                 115 ctg tag cac cgc cta cat acc tcg ctc tgc taa tcc tgt tac cag tgg     432
Leu     His Arg Leu His Thr Ser Leu Cys     Ser Cys Tyr Gln Trp
120                 125                     130 ctg ctg cca gtg gcg ata agt cgt gtc tta ccg ggt tgg act caa gac     480
Leu Leu Pro Val Ala Ile Ser Arg Val Leu Pro Gly Trp Thr Gln Asp
    135                 140                 145
```

```
gat agt tac cgg ata agg cgc agc ggt cgg gct gaa cgg ggg gtt cgt      528
Asp Ser Tyr Arg Ile Arg Arg Ser Gly Arg Ala Glu Arg Gly Val Arg
150             155                 160                 165 gca cac agc cca gct tgg agc gaa cga cct aca ccg aac tga gat acc      576
Ala His Ser Pro Ala Trp Ser Glu Arg Pro Thr Pro Asn     Asp Thr
            170                 175                         180 tac agc gtg agc tat gag aaa gcg cca cgc ttc ccg aag gga gaa agg      624
Tyr Ser Val Ser Tyr Glu Lys Ala Pro Arg Phe Pro Lys Gly Glu Arg
                185                 190                 195 cgg aca ggt atc cgg taa gcg gca ggg tcg gaa cag gag agc gca cga      672
Arg Thr Gly Ile Arg     Ala Ala Gly Ser Glu Gln Glu Ser Ala Arg
                200                 205                 210 ggg agc ttc cag ggg gaa acg cct ggt atc ttt ata gtc ctg tcg ggt      720
Gly Ser Phe Gln Gly Glu Thr Pro Gly Ile Phe Ile Val Leu Ser Gly
            215                 220                 225 ttc gcc acc tct gac ttg agc gtc gat ttt tgt gat gct cgt cag ggg      768
Phe Ala Thr Ser Asp Leu Ser Val Asp Phe Cys Asp Ala Arg Gln Gly
                230                 235                 240 ggc gga gcc tat gga aaa acg cca gca acg cgg cct ttt tac ggt tcc      816
Gly Gly Ala Tyr Gly Lys Thr Pro Ala Thr Arg Pro Phe Tyr Gly Ser
245             250                 255 tgg cct ttt gct ggc ctt ttg ctc aca tgt tct ttc ctg cgt tat ccc      864
Trp Pro Phe Ala Gly Leu Leu Leu Thr Cys Ser Phe Leu Arg Tyr Pro
260             265                 270                 275 ctg att ctg tgg ata acc gta tta ccg cct ttg agt gag ctg ata ccg      912
Leu Ile Leu Trp Ile Thr Val Leu Pro Pro Leu Ser Glu Leu Ile Pro
                280                 285                 290 ctc gcc gca gcc gaa cga ccg agc gca gcg agt cag tga gcg agg aag      960
Leu Ala Ala Ala Glu Arg Pro Ser Ala Ala Ser Gln     Ala Arg Lys
            295                 300                     305 cgg aag agc gcc caa tac gca aac cgc ctc tcc ccg cgc gtt ggc cga     1008
Arg Lys Ser Ala Gln Tyr Ala Asn Arg Leu Ser Pro Arg Val Gly Arg
                310                 315                 320 ttc att aat gca gag cgg ccg cct caa ggc gca ctc ccg ttc tgg ata     1056
Phe Ile Asn Ala Glu Arg Pro Pro Gln Gly Ala Leu Pro Phe Trp Ile
                325                 330                 335 atg ttt ttt gcg ccg aca tca taa cgg ttc tgg caa ata ttc tga aat     1104
Met Phe Phe Ala Pro Thr Ser     Arg Phe Trp Gln Ile Phe     Asn
340             345                 350 gag ctg ttg aca att aat cat cga act agt taa cta gta cgc aag ttc     1152
Glu Leu Leu Thr Ile Asn His Arg Thr Ser     Leu Val Arg Lys Phe
            355                 360                 365 acg taa aaa ggg tat cga caa tga aag caa ttt tcg tac tga aag ctt     1200
Thr     Lys Gly Tyr Arg Gln     Lys Gln Phe Ser Tyr     Lys Leu
            370                 375                 380 cta atg atg ata agt tat atc ggg cag att cta gac ctc ctg atg aaa     1248
Leu Met Met Ile Ser Tyr Ile Gly Gln Ile Leu Asp Leu Leu Met Lys
                385                 390                 395 taa agc agt cag gtg gtc tta tgc caa gag gac aga gtg agt act ttg     1296
    Ser Ser Gln Val Val Leu Cys Gln Glu Asp Arg Val Ser Thr Leu
                400                 405                 410 acc gag gta ctc aaa tga ata tca acc ttt atg atc atg caa gag gaa     1344
Thr Glu Val Leu Lys     Ile Ser Thr Phe Met Ile Met Gln Glu Glu
            415                 420                 425 ctc aga cgg gat ttg tta ggc acg atg atg gat atg ttt cca cct caa     1392
Leu Arg Arg Asp Leu Leu Gly Thr Met Met Asp Met Phe Pro Pro Gln
            430                 435                 440 tta gtt tga gaa gtg ccc act tag tgg gtc aaa cta tat tgt ctg gtc     1440
Leu Val     Glu Val Pro Thr     Trp Val Lys Leu Tyr Cys Leu Val
            445                 450                 455
```

```
                                          -continued att cta ctt att ata tat atg tta tag cca ctg cac cca aca tgt tta         1488
Ile Leu Leu Ile Ile Tyr Met Leu     Pro Leu His Pro Thr Cys Leu
            460                 465                 470 acg tta atg atg tat tag ggg cat aca gtc ctc atc cag atg aac aag         1536
Thr Leu Met Met Tyr     Gly His Thr Val Leu Ile Gln Met Asn Lys
            475                 480                 485 aag ttt ctg ctt tag gtg gga ttc cat act ccc aaa tat atg gat ggt         1584
Lys Phe Leu Leu     Val Gly Phe His Thr Pro Lys Tyr Met Asp Gly
            490                 495                 500 atc gag ttc att ttg ggg tgc ttg atg aac aat tac atc gta ata ggg         1632
Ile Glu Phe Ile Leu Gly Cys Leu Met Asn Asn Tyr Ile Val Ile Gly
            505                 510                 515 gct aca gag ata gat att aca gta act tag ata ttg ctc cag cag cag         1680
Ala Thr Glu Ile Asp Ile Thr Val Thr     Ile Leu Leu Gln Gln Gln
            520                 525                 530 atg gtt atg gat tgg cag gtt tcc ctc cgg agc ata gag ctt gga ggg         1728
Met Val Met Asp Trp Gln Val Ser Leu Arg Ser Ile Glu Leu Gly Gly
            535                 540                 545 aag agc cgt gga ttc atc atg cac cgc cgg gtt gtg gga atg ctc caa         1776
Lys Ser Arg Gly Phe Ile Met His Arg Arg Val Val Gly Met Leu Gln
            550                 555                 560 gat cat cgg gat ccg gga aga cac ccg aga tct ccc agg ctg ttc acg         1824
Asp His Arg Asp Pro Gly Arg His Pro Arg Ser Pro Arg Leu Phe Thr
565                 570                 575                 580 ctg ctc acg ctg aaa tca acg aag ctg gtc gtg ccc ccg agg ctg atg         1872
Leu Leu Thr Leu Lys Ser Thr Lys Leu Val Val Pro Pro Arg Leu Met
            585                 590                 595 cgc aac aaa ata act tca aca aag atc aac aaa gcg cct tct atg aaa         1920
Arg Asn Lys Ile Thr Ser Thr Lys Ile Asn Lys Ala Pro Ser Met Lys
            600                 605                 610 tct tga aca tgc cta act taa acg aag cgc aac gta acg gct tca ttc         1968
Ser     Thr Cys Leu Thr     Thr Lys Arg Asn Val Thr Ala Ser Phe
                615                 620                 625 aaa gtc tta aag acg acc caa gcc aaa gca cta acg ttt tag gtg aag         2016
Lys Val Leu Lys Thr Thr Gln Ala Lys Ala Leu Thr Phe     Val Lys
            630                 635                 640 cta aaa aat taa acg aat ctc aag cac cca aac ccg agg ctg atg cgc         2064
Leu Lys Asn     Thr Asn Leu Lys His Pro Asn Pro Arg Leu Met Arg
                645                 650                 655 aac aaa ata act tca aca aag atc aac aaa gcg cct tct atg aaa tct         2112
Asn Lys Ile Thr Ser Thr Lys Ile Asn Lys Ala Pro Ser Met Lys Ser
            660                 665                 670 tga aca tgc cta act taa acg aag cgc aac gta acg gct tca ttc aaa         2160
    Thr Cys Leu Thr     Thr Lys Arg Asn Val Thr Ala Ser Phe Lys
            675                 680                 685 gtc tta aag acg acc caa gcc aaa gca cta acg ttt tag gtg aag cta         2208
Val Leu Lys Thr Thr Gln Ala Lys Ala Leu Thr Phe     Val Lys Leu
            690                 695                 700 aaa aat taa acg aat ctc aag cac cca aac ccg agg tag cag gtc aga         2256
Lys Asn     Thr Asn Leu Lys His Pro Asn Pro Arg     Gln Val Arg
                705                 710                 715 att agc ttg ctg att gat tga ccg gat cga tcc ggc tct aga att aat         2304
Ile Ser Leu Leu Ile Asp     Pro Asp Arg Ser Gly Ser Arg Ile Asn
            720                 725                 730 tca cct cga aag caa gct gat aaa ccg ata caa tta aag gct cct ttt         2352
Ser Pro Arg Lys Gln Ala Asp Lys Pro Ile Gln Leu Lys Ala Pro Phe
            735                 740                 745 gga gcc ttt ttt ttt gga gat ttt caa cgt gaa aaa att att att cgc         2400
Gly Ala Phe Phe Phe Gly Asp Phe Gln Arg Glu Lys Ile Ile Ile Arg
```

-continued

|  |  |  |  |  |  |  |  |  |  |  |  |  |  |
|---|---|---|---|---|---|---|---|---|---|---|---|---|---|
|  |  | 750 |  |  |  | 755 |  |  |  | 760 |  |  |  |
| aat | tca | agc | taa | ttc | acc | tag | aaa | gca | agc | tga | taa | acc | gat aca att | 2448 |
| Asn | Ser | Ser | | Phe | Thr | | Lys | Ala | Ser | | | Thr | Asp Thr Ile | |
|  |  | 765 |  |  |  |  | 770 |  |  |  |  |  |  |
| aaa | ggc | tcc | ttt | tgg | agc | ctt | ttt | ttt | tgg | aga | ttt | tca | acg tga aaa | 2496 |
| Lys | Gly | Ser | Phe | Trp | Ser | Leu | Phe | Phe | Trp | Arg | Phe | Ser | Thr Lys | |
| 775 |  |  |  | 780 |  |  |  |  | 785 |  |  |  |  |
| aat | tat | tat | tcg | caa | ttc | aag | ctc | tgc | ctc | gcg | cgt | ttc | ggt gat gac | 2544 |
| Asn | Tyr | Tyr | Ser | Gln | Phe | Lys | Leu | Cys | Leu | Ala | Arg | Phe | Gly Asp Asp | |
| 790 |  |  |  |  | 795 |  |  |  | 800 |  |  |  | 805 | |
| ggt | gaa | aac | ctc | tga | cac | atg | cag | ctc | ccg | gag | acg | gtc | aca gct tgt | 2592 |
| Gly | Glu | Asn | Leu | | His | Met | Gln | Leu | Pro | Glu | Thr | Val | Thr Ala Cys | |
|  |  |  | 810 |  |  |  |  |  | 815 |  |  |  | 820 | |
| ctg | taa | gcg | gat | gcc | ggg | agc | aga | caa | gcc | cgt | cag | ggc | gcg tca gcg | 2640 |
| Leu | | Ala | Asp | Ala | Gly | Ser | Arg | Gln | Ala | Arg | Gln | Gly | Ala Ser Ala | |
|  |  |  |  | 825 |  |  |  |  | 830 |  |  |  | 835 | |
| ggt | gtt | ggc | ggg | tgt | cgg | ggc | gca | gcc | atg | acc | cag | tca | cgt agc gat | 2688 |
| Gly | Val | Gly | Gly | Cys | Arg | Gly | Ala | Ala | Met | Thr | Gln | Ser | Arg Ser Asp | |
|  |  |  |  | 840 |  |  |  |  | 845 |  |  |  | 850 | |
| agc | gga | gtg | tat | gtg | tct | caa | aat | ctc | tga | tgt | tac | att | gca caa gat | 2736 |
| Ser | Gly | Val | Tyr | Val | Ser | Gln | Asn | Leu | | Cys | Tyr | Ile | Ala Gln Asp | |
|  |  |  | 855 |  |  |  |  | 860 |  |  |  |  | 865 | |
| aaa | aat | ata | tca | tca | tga | aca | ata | aaa | ctg | tct | gct | tac | ata aac agt | 2784 |
| Lys | Asn | Ile | Ser | Ser | | Thr | Ile | Lys | Leu | Ser | Ala | Tyr | Ile Asn Ser | |
|  |  |  | 870 |  |  |  |  | 875 |  |  |  |  | 880 | |
| aat | aca | agg | ggt | gtt | atg | agc | cat | att | caa | cgg | gaa | acg | tct tgc tcg | 2832 |
| Asn | Thr | Arg | Gly | Val | Met | Ser | His | Ile | Gln | Arg | Glu | Thr | Ser Cys Ser | |
|  |  |  | 885 |  |  |  |  | 890 |  |  |  |  | 895 | |
| agg | ccg | cga | tta | aat | tcc | aac | atg | gat | gct | gat | tta | tat | ggg tat aaa | 2880 |
| Arg | Pro | Arg | Leu | Asn | Ser | Asn | Met | Asp | Ala | Asp | Leu | Tyr | Gly Tyr Lys | |
|  |  | 900 |  |  |  |  | 905 |  |  |  |  | 910 | | |
| tgg | gct | cgc | gat | aat | gtc | ggg | caa | tca | ggt | gcg | aca | atc | tat cga ttg | 2928 |
| Trp | Ala | Arg | Asp | Asn | Val | Gly | Gln | Ser | Gly | Ala | Thr | Ile | Tyr Arg Leu | |
|  |  | 915 |  |  |  |  | 920 |  |  |  |  | 925 | | |
| tat | ggg | aag | ccc | gat | gcg | cca | gag | ttg | ttt | ctg | aaa | cat | ggc aaa ggt | 2976 |
| Tyr | Gly | Lys | Pro | Asp | Ala | Pro | Glu | Leu | Phe | Leu | Lys | His | Gly Lys Gly | |
| 930 |  |  |  |  | 935 |  |  |  |  | 940 |  |  |  | 945 |
| agc | gtt | gcc | aat | gat | gtt | aca | gat | gag | atg | gtc | aga | cta | aac tgg ctg | 3024 |
| Ser | Val | Ala | Asn | Asp | Val | Thr | Asp | Glu | Met | Val | Arg | Leu | Asn Trp Leu | |
|  |  |  |  | 950 |  |  |  |  | 955 |  |  |  | 960 | |
| acg | gaa | ttt | atg | cct | ctt | ccg | acc | atc | aag | cat | ttt | atc | cgt act cct | 3072 |
| Thr | Glu | Phe | Met | Pro | Leu | Pro | Thr | Ile | Lys | His | Phe | Ile | Arg Thr Pro | |
|  |  |  | 965 |  |  |  |  | 970 |  |  |  |  | 975 | |
| gat | gat | gca | tgg | tta | ctc | acc | act | gcg | atc | ccc | ggg | aaa | aca gca ttc | 3120 |
| Asp | Asp | Ala | Trp | Leu | Leu | Thr | Thr | Ala | Ile | Pro | Gly | Lys | Thr Ala Phe | |
|  |  |  | 980 |  |  |  |  | 985 |  |  |  |  | 990 | |
| cag | gta | tta | gaa | gaa | tat | cct | gat | tca | ggt | gaa | aat | | att gtt gat gcg | 3168 |
| Gln | Val | Leu | Glu | Glu | Tyr | Pro | Asp | Ser | Gly | Glu | Asn | | Ile Val Asp Ala | |
|  |  | 995 |  |  |  |  | 1000 |  |  |  |  | 1005 | | |
| ctg | gca | gtg | ttc | ctg | cgc | cgg | ttg | cat | tcg | att | | cct | gtt tgt aat | 3213 |
| Leu | Ala | Val | Phe | Leu | Arg | Arg | Leu | His | Ser | Ile | | Pro | Val Cys Asn | |
| 1010 |  |  |  |  | 1015 |  |  |  |  | 1020 |  |  |  | |
| tgt | cct | ttt | aac | agc | gat | cgc | gta | ttt | cgt | ctc | | gct | cag gcg caa | 3258 |
| Cys | Pro | Phe | Asn | Ser | Asp | Arg | Val | Phe | Arg | Leu | | Ala | Gln Ala Gln | |
| 1025 |  |  |  |  | 1030 |  |  |  |  | 1035 |  |  |  | |
| tca | cga | atg | aat | aac | ggt | ttg | gtt | gat | gcg | agt | | gat | ttt gag acg | 3303 |
| Ser | Arg | Met | Asn | Asn | Gly | Leu | Val | Asp | Ala | Ser | | Asp | Phe Glu Thr | |
| 1040 |  |  |  |  | 1045 |  |  |  |  | 1050 |  |  |  | |
| agc | gta | atg | gct | ggc | ctg | ttg | aac | aag | tct | gga | | aag | aaa tgc ata | 3348 |

```
Ser  Val  Met  Ala  Gly  Leu  Leu  Asn  Lys  Ser  Gly  Lys  Lys  Cys  Ile
1055                1060                1065 aac  ttt  tgc  cat  tct  cac  cgg  att  cag  tcg  tca  ctc  atg  gtg  att         3393
Asn  Phe  Cys  His  Ser  His  Arg  Ile  Gln  Ser  Ser  Leu  Met  Val  Ile
1070                1075                1080 tct  cac  ttg  ata  acc  tta  ttt  ttg  acg  agg  gga  aat  taa  tag  gtt         3438
Ser  His  Leu  Ile  Thr  Leu  Phe  Leu  Thr  Arg  Gly  Asn            Val
1085                1090                1095 gta  ttg  atg  ttg  gac  gag  tcg  gaa  tcg  cag  acc  gat  acc  agg  atc         3483
Val  Leu  Met  Leu  Asp  Glu  Ser  Glu  Ser  Gln  Thr  Asp  Thr  Arg  Ile
          1100                1105                1110 ttg  cca  tcc  tat  gga  act  gcc  tcg  gtg  agt  ttt  ctc  ctt  cat  tac         3528
Leu  Pro  Ser  Tyr  Gly  Thr  Ala  Ser  Val  Ser  Phe  Leu  Leu  His  Tyr
          1115                1120                1125 aga  aac  ggc  ttt  ttc  aaa  aat  atg  gta  ttg  ata  atc  ctg  ata  tga         3573
Arg  Asn  Gly  Phe  Phe  Lys  Asn  Met  Val  Leu  Ile  Ile  Leu  Ile
          1130                1135                1140 ata  aat  tgc  agt  ttc  att  tga  tgc  tcg  atg  agt  ttt  tct  aat  cag         3618
Ile  Asn  Cys  Ser  Phe  Ile       Cys  Ser  Met  Ser  Phe  Ser  Asn  Gln
               1145                     1150                          1155 aat  tgg  tta  att  ggt  tgt  aac  act  ggc  aga  gca  tta  cgc  tga  ctt         3663
Asn  Trp  Leu  Ile  Gly  Cys  Asn  Thr  Gly  Arg  Ala  Leu  Arg       Leu
               1160                     1165 gac  ggg  acg  gcg  gct  ttg  ttg  aat  aaa  tcg  aac  ttt  tgc  tga  gtt         3708
Asp  Gly  Thr  Ala  Ala  Leu  Leu  Asn  Lys  Ser  Asn  Phe  Cys       Val
1170                1175                1180 gaa  gga  tca  gat  cac  gca  tct  tcc  cga  caa  cgc  aga  ccg  ttc  cgt         3753
Glu  Gly  Ser  Asp  His  Ala  Ser  Ser  Arg  Gln  Arg  Arg  Pro  Phe  Arg
     1185                1190                1195 ggc  aaa  gca  aaa  gtt  caa  aat  cac  caa  ctg  gtc  cgg  atc  gat  ccg         3798
Gly  Lys  Ala  Lys  Val  Gln  Asn  His  Gln  Leu  Val  Arg  Ile  Asp  Pro
     1200                1205                1210

<210> SEQ ID NO 4
<211> LENGTH: 1213
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 4

Val  Pro  His  Leu  Ser  Ile  Gly  Asn  Cys  Gln  Thr  Lys  Phe  Thr  His  Ile
1                   5                   10                  15

Tyr  Phe  Arg  Leu  Ile  Asn  Phe  Ile  Phe  Asn  Leu  Lys  Gly  Ser  Arg  Arg
               20                  25                  30

Ser  Phe  Leu  Ile  Ile  Ser  Pro  Lys  Ser  Leu  Asn  Val  Ser  Phe  Arg  Ser
          35                  40                  45

Thr  Glu  Arg  Gln  Thr  Pro  Lys  Arg  Ser  Lys  Asp  Leu  Leu  Glu  Ile  Leu
     50                  55                  60

Phe  Phe  Cys  Ala  Ser  Ala  Ala  Cys  Lys  Gln  Lys  Asn  His  Arg  Tyr  Gln
65                  70                  75                  80

Arg  Trp  Phe  Val  Cys  Arg  Ile  Lys  Ser  Tyr  Gln  Leu  Phe  Phe  Arg  Arg
               85                  90                  95

Leu  Ala  Ser  Ala  Glu  Arg  Arg  Tyr  Gln  Ile  Leu  Ser  Phe  Cys  Ser  Arg
          100                 105                 110

Ser  Ala  Thr  Thr  Ser  Arg  Thr  Leu  His  Arg  Leu  His  Thr  Ser  Leu  Cys
     115                 120                 125

Ser  Cys  Tyr  Gln  Trp  Leu  Leu  Pro  Val  Ala  Ile  Ser  Arg  Val  Leu  Pro
```

-continued

```
            130                 135                 140
Gly Trp Thr Gln Asp Asp Ser Tyr Arg Ile Arg Arg Ser Gly Arg Ala
145                 150                 155                 160

Glu Arg Gly Val Arg Ala His Ser Pro Ala Trp Ser Glu Arg Pro Thr
                165                 170                 175

Pro Asn Asp Thr Tyr Ser Val Ser Tyr Glu Lys Ala Pro Arg Phe Pro
                180                 185                 190

Lys Gly Glu Arg Arg Thr Gly Ile Arg Ala Ala Gly Ser Glu Gln Glu
                195                 200                 205

Ser Ala Arg Gly Ser Phe Gln Gly Glu Thr Pro Gly Ile Phe Ile Val
210                 215                 220

Leu Ser Gly Phe Ala Thr Ser Asp Leu Ser Val Asp Phe Cys Asp Ala
225                 230                 235                 240

Arg Gln Gly Gly Gly Ala Tyr Gly Lys Thr Pro Ala Thr Arg Pro Phe
                245                 250                 255

Tyr Gly Ser Trp Pro Phe Ala Gly Leu Leu Leu Thr Cys Ser Phe Leu
                260                 265                 270

Arg Tyr Pro Leu Ile Leu Trp Ile Thr Val Leu Pro Pro Leu Ser Glu
                275                 280                 285

Leu Ile Pro Leu Ala Ala Ala Glu Arg Pro Ser Ala Ala Ser Gln Ala
                290                 295                 300

Arg Lys Arg Lys Ser Ala Gln Tyr Ala Asn Arg Leu Ser Pro Arg Val
305                 310                 315                 320

Gly Arg Phe Ile Asn Ala Glu Arg Pro Pro Gln Gly Ala Leu Pro Phe
                325                 330                 335

Trp Ile Met Phe Phe Ala Pro Thr Ser Arg Phe Trp Gln Ile Phe Asn
                340                 345                 350

Glu Leu Leu Thr Ile Asn His Arg Thr Ser Leu Val Arg Lys Phe Thr
                355                 360                 365

Lys Gly Tyr Arg Gln Lys Gln Phe Ser Tyr Lys Leu Leu Met Met Ile
                370                 375                 380

Ser Tyr Ile Gly Gln Ile Leu Asp Leu Leu Met Lys Ser Ser Gln Val
385                 390                 395                 400

Val Leu Cys Gln Glu Asp Arg Val Ser Thr Leu Thr Glu Val Leu Lys
                405                 410                 415

Ile Ser Thr Phe Met Ile Met Gln Glu Leu Arg Arg Asp Leu Leu
                420                 425                 430

Gly Thr Met Met Asp Met Phe Pro Pro Gln Leu Val Glu Val Pro Thr
                435                 440                 445

Trp Val Lys Leu Tyr Cys Leu Val Ile Leu Leu Ile Ile Tyr Met Leu
450                 455                 460

Pro Leu His Pro Thr Cys Leu Thr Leu Met Met Tyr Gly His Thr Val
465                 470                 475                 480

Leu Ile Gln Met Asn Lys Lys Phe Leu Leu Val Gly Phe His Thr Pro
                485                 490                 495

Lys Tyr Met Asp Gly Ile Glu Phe Ile Leu Gly Cys Leu Met Asn Asn
                500                 505                 510

Tyr Ile Val Ile Gly Ala Thr Glu Ile Asp Ile Thr Val Thr Ile Leu
                515                 520                 525

Leu Gln Gln Gln Met Val Met Asp Trp Gln Val Ser Leu Arg Ser Ile
                530                 535                 540

Glu Leu Gly Gly Lys Ser Arg Gly Phe Ile Met His Arg Arg Val Val
545                 550                 555                 560
```

```
Gly Met Leu Gln Asp His Arg Asp Pro Gly Arg His Pro Arg Ser Pro
                565                 570                 575

Arg Leu Phe Thr Leu Leu Thr Leu Lys Ser Thr Lys Leu Val Val Pro
                580                 585                 590

Pro Arg Leu Met Arg Asn Lys Ile Thr Ser Thr Lys Ile Asn Lys Ala
                595                 600                 605

Pro Ser Met Lys Ser Thr Cys Leu Thr Thr Lys Arg Asn Val Thr Ala
            610                 615                 620

Ser Phe Lys Val Leu Lys Thr Thr Gln Ala Lys Ala Leu Thr Phe Val
625                 630                 635                 640

Lys Leu Lys Asn Thr Asn Leu Lys His Pro Asn Pro Arg Leu Met Arg
                645                 650                 655

Asn Lys Ile Thr Ser Thr Lys Ile Asn Lys Ala Pro Ser Met Lys Ser
                660                 665                 670

Thr Cys Leu Thr Thr Lys Arg Asn Val Thr Ala Ser Phe Lys Val Leu
            675                 680                 685

Lys Thr Thr Gln Ala Lys Ala Leu Thr Phe Val Lys Leu Lys Asn Thr
            690                 695                 700

Asn Leu Lys His Pro Asn Pro Arg Gln Val Arg Ile Ser Leu Leu Ile
705                 710                 715                 720

Asp Pro Asp Arg Ser Gly Ser Arg Ile Asn Ser Pro Arg Lys Gln Ala
                725                 730                 735

Asp Lys Pro Ile Gln Leu Lys Ala Pro Phe Gly Ala Phe Phe Phe Gly
                740                 745                 750

Asp Phe Gln Arg Glu Lys Ile Ile Arg Asn Ser Ser Phe Thr Lys
                755                 760                 765

Ala Ser Thr Asp Thr Ile Lys Gly Ser Phe Trp Ser Leu Phe Phe Trp
                770                 775                 780

Arg Phe Ser Thr Lys Asn Tyr Tyr Ser Gln Phe Lys Leu Cys Leu Ala
785                 790                 795                 800

Arg Phe Gly Asp Asp Gly Glu Asn Leu His Met Gln Leu Pro Glu Thr
                805                 810                 815

Val Thr Ala Cys Leu Ala Asp Ala Gly Ser Arg Gln Ala Arg Gln Gly
                820                 825                 830

Ala Ser Ala Gly Val Gly Gly Cys Arg Gly Ala Ala Met Thr Gln Ser
                835                 840                 845

Arg Ser Asp Ser Gly Val Tyr Val Ser Gln Asn Leu Cys Tyr Ile Ala
            850                 855                 860

Gln Asp Lys Asn Ile Ser Ser Thr Ile Lys Leu Ser Ala Tyr Ile Asn
865                 870                 875                 880

Ser Asn Thr Arg Gly Val Met Ser His Ile Gln Arg Glu Thr Ser Cys
                885                 890                 895

Ser Arg Pro Arg Leu Asn Ser Asn Met Asp Ala Asp Leu Tyr Gly Tyr
            900                 905                 910

Lys Trp Ala Arg Asp Asn Val Gly Gln Ser Gly Ala Thr Ile Tyr Arg
            915                 920                 925

Leu Tyr Gly Lys Pro Asp Ala Pro Glu Leu Phe Leu Lys His Gly Lys
            930                 935                 940

Gly Ser Val Ala Asn Asp Val Thr Asp Glu Met Val Arg Leu Asn Trp
945                 950                 955                 960

Leu Thr Glu Phe Met Pro Leu Pro Thr Ile Lys His Phe Ile Arg Thr
                965                 970                 975
```

-continued

```
Pro Asp Asp Ala Trp Leu Leu Thr Thr Ala Ile Pro Gly Lys Thr Ala
            980                 985                 990
Phe Gln Val Leu Glu Glu Tyr Pro Asp Ser Gly Glu Asn Ile Val Asp
            995                1000                1005
Ala Leu Ala Val Phe Leu Arg Arg Leu His Ser Ile Pro Val Cys Asn
        1010                1015                1020
Cys Pro Phe Asn Ser Asp Arg Val Phe Arg Leu Ala Gln Ala Gln Ser
1025                1030                1035                1040
Arg Met Asn Asn Gly Leu Val Asp Ala Ser Asp Phe Glu Thr Ser Val
                1045                1050                1055
Met Ala Gly Leu Leu Asn Lys Ser Gly Lys Lys Cys Ile Asn Phe Cys
            1060                1065                1070
His Ser His Arg Ile Gln Ser Ser Leu Met Val Ile Ser His Leu Ile
            1075                1080                1085
Thr Leu Phe Leu Thr Arg Gly Asn Val Val Leu Met Leu Asp Glu Ser
        1090                1095                1100
Glu Ser Gln Thr Asp Thr Arg Ile Leu Pro Ser Tyr Gly Thr Ala Ser
1105                1110                1115                1120
Val Ser Phe Leu Leu His Tyr Arg Asn Gly Phe Phe Lys Asn Met Val
                1125                1130                1135
Leu Ile Ile Leu Ile Ile Asn Cys Ser Phe Ile Cys Ser Met Ser Phe
            1140                1145                1150
Ser Asn Gln Asn Trp Leu Ile Gly Cys Asn Thr Gly Arg Ala Leu Arg
            1155                1160                1165
Leu Asp Gly Thr Ala Ala Leu Leu Asn Lys Ser Asn Phe Cys Val Glu
        1170                1175                1180
Gly Ser Asp His Ala Ser Ser Arg Gln Arg Pro Phe Arg Gly Lys
1185                1190                1195                1200
Ala Lys Val Gln Asn His Gln Leu Val Arg Ile Asp Pro
                1205                1210

<210> SEQ ID NO 5
<211> LENGTH: 1176
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 5

Cys Leu Thr Asp Ala Leu Val Thr Val Arg Pro Ser Leu Leu Ile Tyr
  1               5                  10                  15
Thr Leu Asp Phe Lys Thr Ser Phe Leu Ile Lys Asp Leu Gly Glu Asp
             20                  25                  30
Pro Phe Ser His Asp Gln Asn Pro Leu Thr Val Phe Val Pro Leu Ser
         35                  40                  45
Val Arg Pro Arg Arg Lys Asp Gln Arg Ile Phe Leu Arg Ser Phe Phe
     50                  55                  60
Ser Ala Arg Asn Leu Leu Leu Ala Asn Lys Lys Thr Thr Ala Thr Ser
 65                  70                  75                  80
Gly Gly Leu Phe Ala Gly Ser Arg Ala Thr Asn Ser Phe Ser Glu Gly
                 85                  90                  95
Asn Trp Leu Gln Gln Ser Ala Asp Thr Lys Tyr Cys Pro Ser Ser Val
            100                 105                 110
Ala Val Val Arg Pro Pro Leu Gln Glu Leu Cys Ser Thr Ala Tyr Ile
        115                 120                 125
```

```
Pro Arg Ser Ala Asn Pro Val Thr Ser Gly Cys Cys Gln Trp Arg Val
    130                 135                 140

Val Ser Tyr Arg Val Gly Leu Lys Thr Ile Val Thr Gly Gly Ala Ala
145                 150                 155                 160

Val Gly Leu Asn Gly Gly Phe Val His Thr Ala Gln Leu Gly Ala Asn
                165                 170                 175

Asp Leu His Arg Thr Glu Ile Pro Thr Ala Ala Met Arg Lys Arg His
            180                 185                 190

Ala Ser Arg Arg Glu Lys Gly Gly Gln Val Ser Gly Lys Arg Gln Gly
        195                 200                 205

Arg Asn Arg Arg Ala His Glu Gly Ala Ser Arg Gly Lys Arg Leu Val
    210                 215                 220

Ser Leu Ser Cys Arg Val Ser Pro Pro Leu Thr Ala Ser Ile Phe Val
225                 230                 235                 240

Met Leu Val Arg Gly Ala Glu Pro Met Glu Lys Arg Gln Gln Arg Gly
                245                 250                 255

Leu Phe Thr Val Pro Gly Leu Leu Ala Phe Cys Ser His Val Leu
            260                 265                 270

Ser Cys Val Ile Pro Phe Cys Gly Pro Tyr Tyr Arg Leu Val Ser Tyr
        275                 280                 285

Arg Ser Pro Gln Pro Asn Asp Arg Ala Gln Arg Val Ser Glu Arg Gly
    290                 295                 300

Ser Gly Arg Ala Pro Asn Thr Gln Thr Ala Ser Pro Arg Ala Leu Ala
305                 310                 315                 320

Asp Ser Leu Met Gln Ser Gly Arg Leu Lys Ala His Ser Arg Ser Gly
                325                 330                 335

Cys Phe Leu Arg Arg His His Asn Gly Ser Gly Lys Tyr Ser Glu Met
            340                 345                 350

Ser Cys Gln Leu Ile Ile Glu Leu Val Asn Tyr Ala Ser Ser Arg Lys
        355                 360                 365

Lys Gly Ile Asp Asn Glu Ser Asn Phe Arg Thr Glu Ser Phe Val Ile
    370                 375                 380

Ser Gly Arg Phe Thr Ser Asn Lys Ala Val Arg Trp Ser Tyr Ala Lys
385                 390                 395                 400

Arg Thr Glu Val Leu Pro Arg Tyr Ser Asn Glu Tyr Gln Pro Leu Ser
                405                 410                 415

Cys Lys Arg Asn Ser Asp Gly Ile Cys Ala Arg Trp Ile Cys Phe His
            420                 425                 430

Leu Asn Phe Glu Lys Cys Pro Leu Ser Gly Ser Asn Tyr Ile Val Trp
        435                 440                 445

Ser Phe Tyr Leu Leu Tyr Ile Cys Tyr Ser His Cys Thr Gln His Val
    450                 455                 460

Arg Cys Ile Arg Gly Ile Gln Ser Ser Arg Thr Arg Ser Phe Cys
465                 470                 475                 480

Phe Arg Trp Asp Ser Ile Leu Pro Asn Ile Trp Met Val Ser Ser Ser
                485                 490                 495

Phe Trp Gly Ala Thr Ile Thr Ser Gly Leu Gln Arg Ile Leu Gln Leu
            500                 505                 510

Arg Tyr Cys Ser Ser Ser Arg Trp Leu Trp Ile Gly Arg Phe Pro Ser
        515                 520                 525

Gly Ala Ser Leu Glu Gly Arg Ala Val Asp Ser Ser Cys Thr Ala Gly
    530                 535                 540
```

-continued

```
Leu Trp Glu Cys Ser Lys Ile Ile Gly Ile Arg Glu Asp Thr Arg Asp
545                 550                 555                 560

Leu Pro Gly Cys Ser Arg Cys Ser Arg Asn Gln Arg Ser Trp Ser Cys
                565                 570                 575

Pro Arg Gly Cys Ala Thr Lys Leu Gln Gln Arg Ser Thr Lys Arg Leu
            580                 585                 590

Leu Asn Leu Glu His Ala Leu Lys Arg Ser Ala Thr Arg Leu His Ser
        595                 600                 605

Lys Ser Arg Arg Pro Lys Pro Lys His Arg Phe Arg Ser Lys Ile Lys
    610                 615                 620

Arg Ile Ser Ser Thr Gln Thr Arg Gly Cys Ala Thr Lys Leu Gln Gln
625                 630                 635                 640

Arg Ser Thr Lys Arg Leu Leu Asn Leu Glu His Ala Leu Lys Arg Ser
                645                 650                 655

Ala Thr Arg Leu His Ser Lys Ser Arg Arg Pro Lys Pro Lys His Arg
            660                 665                 670

Phe Arg Ser Lys Ile Lys Arg Ile Ser Ser Thr Gln Thr Arg Gly Ser
        675                 680                 685

Arg Ser Glu Leu Ala Cys Leu Ile Asp Arg Ile Asp Pro Ala Leu Glu
    690                 695                 700

Leu Ile His Leu Glu Ser Lys Leu Ile Asn Arg Tyr Asn Arg Leu Leu
705                 710                 715                 720

Leu Glu Pro Phe Phe Leu Glu Ile Phe Asn Val Lys Lys Leu Leu Phe
                725                 730                 735

Ala Ile Gln Ala Asn Ser Pro Arg Lys Gln Ala Asp Lys Pro Ile Gln
            740                 745                 750

Leu Lys Ala Pro Phe Gly Ala Phe Phe Gly Asp Phe Gln Arg Glu
        755                 760                 765

Lys Ile Ile Ile Arg Asn Ser Ser Ala Ser Arg Val Ser Val Met
    770                 775                 780

Thr Val Lys Thr Ser Asp Thr Cys Ser Ser Arg Arg Ser Gln Leu
785                 790                 795                 800

Val Cys Lys Arg Met Pro Gly Ala Asp Lys Pro Val Arg Ala Arg Gln
                805                 810                 815

Arg Val Leu Ala Gly Val Gly Ala Gln Pro Pro Ser His Val Ala Ile
            820                 825                 830

Ala Glu Cys Met Cys Leu Lys Ile Ser Asp Val Thr Leu His Lys Ile
        835                 840                 845

Lys Ile Tyr His His Glu Gln Asn Cys Leu Leu Thr Thr Val Ile Gln
    850                 855                 860

Gly Val Leu Ala Ile Phe Asn Gly Lys Arg Leu Ala Arg Gly Arg Asp
865                 870                 875                 880

Ile Pro Thr Trp Met Leu Ile Tyr Met Gly Ile Asn Gly Leu Ala Ile
                885                 890                 895

Met Ser Gly Asn Gln Val Arg Gln Ser Ile Asp Cys Met Gly Ser Pro
            900                 905                 910

Met Arg Gln Ser Cys Phe Asn Met Ala Lys Val Ala Leu Pro Met Met
        915                 920                 925

Leu Gln Met Arg Trp Ser Asp Thr Gly Arg Asn Leu Cys Leu Phe Arg
    930                 935                 940

Pro Ser Ser Ile Leu Ser Val Leu Leu Met Met His Gly Tyr Ser Pro
945                 950                 955                 960

Leu Arg Ser Pro Gly Lys Gln His Ser Arg Tyr Lys Asn Ile Leu Ile
```

-continued

```
                965                 970                 975
Gln Val Lys Ile Leu Leu Met Arg Trp Gln Cys Ser Cys Ala Gly Cys
            980                 985                 990
Ile Arg Phe Leu Phe Val Ile Val Leu Leu Thr Ala Ile Ala Tyr Phe
            995                1000                1005
Val Ser Leu Arg Arg Asn His Glu Ile Thr Val Trp Leu Met Arg Val
           1010                1015                1020
Ile Leu Arg Arg Ala Trp Leu Ala Cys Thr Ser Leu Glu Arg Asn Ala
1025                1030                1035                1040
Thr Phe Ala Ile Leu Thr Gly Phe Ser Arg His Ser Trp Phe Leu Thr
           1045                1050                1055
Pro Tyr Phe Arg Gly Glu Ile Asn Arg Leu Tyr Cys Trp Thr Ser Arg
           1060                1065                1070
Asn Arg Arg Pro Ile Pro Gly Ser Cys His Pro Met Glu Leu Pro Arg
           1075                1080                1085
Val Phe Ser Phe Ile Thr Glu Thr Ala Phe Ser Lys Ile Trp Tyr Ser
           1090                1095                1100
Tyr Glu Ile Ala Val Ser Phe Asp Ala Arg Val Phe Leu Ile Arg Ile
1105                1110                1115                1120
Gly Leu Val Val Thr Leu Ala Glu His Tyr Ala Asp Leu Thr Gly Arg
           1125                1130                1135
Arg Leu Cys Ile Asn Arg Thr Phe Ala Glu Leu Lys Asp Gln Ile Thr
           1140                1145                1150
His Leu Pro Asp Asn Ala Asp Arg Ser Val Ala Lys Gln Lys Phe Lys
           1155                1160                1165
Ile Thr Asn Trp Ser Gly Ser Ile
           1170                1175

<210> SEQ ID NO 6
<211> LENGTH: 1209
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 6

Ala Ser Leu Ile Lys His Trp Leu Ser Asp Gln Val Tyr Ser Tyr Ile
  1               5                  10                  15
Leu Ile Asp Leu Lys Leu His Phe Phe Lys Arg Ile Val Lys Ile Leu
             20                  25                  30
Phe Asp Asn Leu Met Thr Lys Ile Pro Arg Glu Phe Ser Phe His Ala
         35                  40                  45
Ser Asp Pro Val Glu Lys Ile Lys Gly Ser Ser Asp Pro Phe Phe Leu
     50                  55                  60
Arg Val Ile Cys Cys Leu Gln Thr Lys Lys Pro Pro Leu Pro Ala Val
 65                  70                  75                  80
Val Cys Leu Pro Asp Gln Glu Leu Pro Thr Leu Phe Pro Lys Val Thr
                 85                  90                  95
Gly Phe Ser Arg Ala Gln Ile Pro Asn Thr Val Leu Leu Val Pro Leu
            100                 105                 110
Gly His His Phe Lys Asn Ser Val Ala Pro Pro Thr Tyr Leu Ala Leu
            115                 120                 125
Leu Ile Leu Leu Pro Val Ala Ala Ala Ser Gly Asp Lys Ser Cys Leu
        130                 135                 140
```

-continued

```
Thr Gly Leu Asp Ser Arg Arg Leu Pro Asp Lys Ala Gln Arg Ser Gly
145                 150                 155                 160

Thr Gly Gly Ser Cys Thr Gln Pro Ser Leu Glu Arg Thr Thr Tyr Thr
                165                 170                 175

Glu Leu Arg Tyr Leu Gln Arg Glu Leu Glu Ser Ala Thr Leu Pro Glu
            180                 185                 190

Gly Arg Lys Ala Asp Arg Tyr Pro Val Ser Gly Arg Val Gly Thr Gly
        195                 200                 205

Glu Arg Thr Arg Glu Leu Pro Gly Gly Asn Ala Trp Tyr Leu Tyr Ser
    210                 215                 220

Pro Val Gly Phe Arg His Leu Leu Glu Arg Arg Phe Leu Cys Ser Ser
225                 230                 235                 240

Gly Gly Arg Ser Leu Trp Lys Asn Ala Ser Asn Ala Ala Phe Leu Arg
                245                 250                 255

Phe Leu Ala Phe Cys Trp Pro Phe Ala His Met Phe Phe Pro Ala Leu
            260                 265                 270

Ser Pro Asp Ser Val Asp Asn Arg Ile Thr Ala Phe Glu Ala Asp Thr
        275                 280                 285

Ala Arg Arg Ser Arg Thr Thr Glu Arg Ser Glu Ser Val Ser Glu Glu
    290                 295                 300

Ala Glu Glu Arg Pro Ile Arg Lys Pro Pro Leu Pro Ala Arg Trp Pro
305                 310                 315                 320

Ile His Cys Arg Ala Ala Ala Ser Arg Arg Thr Pro Val Leu Asp Asn
                325                 330                 335

Val Phe Cys Ala Asp Ile Ile Thr Val Leu Ala Asn Ile Leu Lys Ala
            340                 345                 350

Val Asp Asn Ser Ser Asn Leu Thr Ser Thr Gln Val His Val Lys Arg
        355                 360                 365

Val Ser Thr Met Lys Ala Ile Phe Val Leu Lys Ala Ser Asn Asp Asp
    370                 375                 380

Lys Leu Tyr Arg Ala Asp Ser Arg Pro Pro Asp Glu Ile Lys Gln Ser
385                 390                 395                 400

Gly Gly Leu Met Pro Arg Gly Gln Ser Glu Tyr Phe Asp Arg Gly Thr
                405                 410                 415

Gln Met Asn Ile Asn Leu Tyr Asp His Ala Arg Gly Thr Gln Thr Gly
            420                 425                 430

Phe Val Arg His Asp Asp Gly Tyr Val Ser Thr Ser Ile Ser Leu Arg
        435                 440                 445

Ser Ala His Leu Val Gly Gln Thr Ile Leu Ser Gly His Ser Thr Tyr
    450                 455                 460

Tyr Ile Tyr Val Ile Ala Thr Ala Pro Asn Met Phe Asn Val Asn Asp
465                 470                 475                 480

Val Leu Gly Ala Tyr Ser Pro His Pro Asp Glu Gln Glu Val Ser Ala
                485                 490                 495

Leu Gly Gly Ile Pro Tyr Ser Gln Ile Tyr Gly Trp Tyr Arg Val His
            500                 505                 510

Phe Gly Val Leu Asp Glu Gln Leu His Arg Asn Arg Gly Tyr Arg Asp
        515                 520                 525

Arg Tyr Tyr Ser Asn Leu Asp Ile Ala Pro Ala Asp Gly Tyr Gly
    530                 535                 540

Leu Ala Gly Phe Pro Pro Glu His Arg Ala Trp Arg Glu Glu Pro Trp
545                 550                 555                 560

Ile His His Ala Pro Pro Gly Cys Gly Asn Ala Pro Arg Ser Ser Gly
```

-continued

```
                565                 570                 575
Ser Gly Lys Thr Pro Glu Ile Ser Gln Ala Val His Ala His Ala
                580                 585                 590
Glu Ile Asn Glu Ala Gly Arg Ala Pro Glu Ala Asp Ala Gln Gln Asn
                595                 600                 605
Asn Phe Asn Lys Asp Gln Gln Ser Ala Phe Tyr Glu Ile Leu Asn Met
            610                 615                 620
Pro Asn Leu Asn Glu Ala Gln Arg Asn Gly Phe Ile Gln Ser Leu Lys
625                 630                 635                 640
Asp Asp Pro Ser Gln Ser Thr Asn Val Leu Gly Glu Ala Lys Lys Leu
                645                 650                 655
Asn Glu Ser Gln Ala Pro Lys Pro Glu Ala Asp Ala Gln Gln Asn Asn
            660                 665                 670
Phe Asn Lys Asp Gln Gln Ser Ala Phe Tyr Glu Ile Leu Asn Met Pro
        675                 680                 685
Asn Leu Asn Glu Ala Gln Arg Asn Gly Phe Ile Gln Ser Leu Lys Asp
            690                 695                 700
Asp Pro Ser Gln Ser Thr Asn Val Leu Gly Glu Ala Lys Lys Leu Asn
705                 710                 715                 720
Glu Ser Gln Ala Pro Lys Pro Glu Val Ala Gly Gln Asn Leu Ala Asp
                725                 730                 735
Leu Thr Gly Ser Ile Arg Leu Asn Phe Thr Ser Lys Ala Ser Thr Asp
                740                 745                 750
Thr Ile Lys Gly Ser Phe Trp Ser Leu Phe Phe Trp Arg Phe Ser Thr
                755                 760                 765
Lys Asn Tyr Tyr Ser Gln Phe Lys Leu Ile His Leu Glu Ser Lys Leu
                770                 775                 780
Ile Asn Arg Tyr Asn Arg Leu Leu Leu Glu Pro Phe Phe Leu Glu Ile
785                 790                 795                 800
Phe Asn Val Lys Lys Leu Leu Phe Ala Ile Gln Ala Leu Pro Arg Ala
                805                 810                 815
Phe Arg Arg Lys Pro Leu Thr His Ala Ala Pro Gly Asp Gly His Ser
                820                 825                 830
Leu Ser Val Ser Gly Cys Arg Glu Gln Thr Ser Pro Ser Gly Arg Val
                835                 840                 845
Ser Gly Cys Trp Arg Val Ser Arg Ser His Asp Pro Val Thr Arg
            850                 855                 860
Arg Ser Val Cys Val Ser Lys Ser Leu Met Leu His Cys Thr Arg Lys
865                 870                 875                 880
Tyr Ile Ile Met Asn Asn Lys Thr Val Cys Leu His Lys Gln Tyr Lys
                885                 890                 895
Gly Cys Tyr Glu Pro Tyr Ser Thr Gly Asn Val Leu Leu Glu Ala Ala
            900                 905                 910
Ile Lys Phe Gln His Gly Cys Phe Ile Trp Val Met Gly Ser Arg Cys
        915                 920                 925
Arg Ala Ile Arg Cys Asp Asn Leu Ser Ile Val Trp Glu Ala Arg Cys
    930                 935                 940
Ala Arg Val Val Ser Glu Thr Trp Gln Arg Arg Cys Gln Cys Tyr Arg
945                 950                 955                 960
Asp Gly Gln Thr Lys Leu Ala Asp Gly Ile Tyr Ala Ser Ser Asp His
                965                 970                 975
Gln Ala Phe Tyr Pro Tyr Ser Cys Met Val Thr His His Cys Asp Pro
            980                 985                 990
```

-continued

```
Arg Glu Asn Ser Ile Pro Gly Ile Arg Arg Ile Ser Phe Arg Lys Tyr
            995                 1000                1005
Cys Cys Ala Gly Ser Val Pro Ala Pro Val Ala Phe Asp Ser Cys Leu
        1010                1015                1020
Leu Ser Phe Gln Arg Ser Arg Ile Ser Ser Arg Ser Gly Ala Ile Thr
1025                1030                1035                1040
Asn Glu Arg Phe Gly Cys Glu Phe Asp Glu Arg Asn Gly Trp Pro Val
                1045                1050                1055
Glu Gln Val Trp Lys Glu Met His Lys Leu Leu Pro Phe Ser Pro Asp
            1060                1065                1070
Ser Val Val Thr His Gly Asp Phe Ser Leu Asp Asn Leu Ile Phe Asp
        1075                1080                1085
Glu Gly Lys Leu Ile Gly Cys Ile Asp Val Gly Arg Val Gly Ile Ala
        1090                1095                1100
Asp Arg Tyr Gln Asp Leu Ala Ile Leu Trp Asn Cys Leu Gly Glu Phe
1105                1110                1115                1120
Ser Pro Ser Leu Gln Lys Arg Leu Phe Gln Lys Tyr Gly Ile Asp Asn
                1125                1130                1135
Pro Asp Met Asn Lys Leu Gln Phe His Leu Met Leu Asp Glu Phe Phe
                1140                1145                1150
Ser Glu Leu Val Asn Trp Leu His Trp Gln Ser Ile Thr Leu Thr Arg
            1155                1160                1165
Asp Gly Gly Phe Val Glu Ile Glu Leu Leu Leu Ser Arg Ile Arg Ser
        1170                1175                1180
Arg Ile Phe Pro Thr Thr Gln Thr Val Pro Trp Gln Ser Lys Ser Ser
1185                1190                1195                1200
Lys Ser Pro Thr Gly Pro Asp Arg Ser
                1205
```

The invention claimed is:

1. An immunogenic complex comprising:
   at least one glycoside and at least one lipid, integrated into an iscom complex or matrix;
   at least one antigen integrated into the iscom complex or coupled onto or mixed with the iscom complex or iscom matrix complex; and
   an adjuvant comprising
   (i) an isolated subunit of an A1 subunit of a bacterial enterotoxin selected from the group consisting of cholera toxin and *E. coli* heat labile enterotoxin, and
   (ii) a fragment of protein A comprising the D region of protein A, said fragment having the ability to bind to Ig or Fc receptors on an antigen-presenting cell.

2. The immunogenic complex according to claim 1, characterised in that said antigen-presenting cell expresses MHC Class I or Class II antigen wherein said antigen-presenting cell is selected from the group consisting of lymphocytes, macrophages, dendritic cells, Langerhans cells and epithelial cells.

3. The immunogenic complex according to claim 1, characterised in that the isolated subunit of an A1 subunit of a bacterial enterotoxin is integrated into an iscom complex comprising at least one glycoside, at least one lipid and at least one antigen.

4. The immunogenic complex according to claim 1, characterised in that said fragment of protein A is integrated into an iscom complex comprising at least one glycoside, at least one lipid and at least one antigen.

5. The immunogenic complex according to claim 1, characterised in that said bacterial A1 enterotoxin subunit is the A1 subunit of cholera toxin.

6. The immunogenic complex according to claim 2, characterised in that the antigen-presenting cell is a lymphocyte.

7. The immunogenic complex according to claim 1, characterised in that the bacterial A1 enterotoxin subunit and said fragment of protein A are bound together into a fusion protein, which is integrated into an iscom complex or coupled onto or mixed with an iscom complex or iscom matrix complex.

8. The immunogenic complex according to claim 1, characterised in that the bacterial A1 enterotoxin subunit, said fragment of protein A and an antigen are bound together into a fusion protein, which is integrated into an iscom complex or coupled onto or mixed with an iscom complex or iscom matrix complex.

9. The immunogenic complex according to claim 7, characterised in that the fusion protein comprises the A1 subunit of cholera toxin fused to one or more copies of said fragment of protein A.

10. An immunogenic composition comprising the immunogenic complex according to claim 1, characterised in that it further comprises one or more excipients that are acceptable in pharmaceutical or veterinary products.

11. The immunogenic complex according to claim 1, characterised in that said fragment is a dimer of the D-region of protein A.

12. The immunogenic complex according to claim 11, characterised in that said adjuvant is a fusion protein CTA1-DD.

13. The immunogenic complex according to claim 12, characterised in that said antigen is an OVA 323-339 peptide epitope and said adjuvant is CTA1-DD linked to the OVA 323-339 peptide epitope.

* * * * *